(12) United States Patent
Bordon-Pallier et al.

(10) Patent No.: US 7,041,824 B2
(45) Date of Patent: May 9, 2006

(54) PURINE DERIVATIVES, PREPARATION METHOD AND USE AS MEDICINES

(75) Inventors: Florence Bordon-Pallier, Guyancourt (FR); Jean-Luc Haesslein, Courtry (FR)

(73) Assignee: Aventis Pharma S.A., Antony (FR)

( * ) Notice: Subject to any disclaimer, the term of this patent is extended or adjusted under 35 U.S.C. 154(b) by 298 days.

(21) Appl. No.: 10/606,424

(22) Filed: Jun. 26, 2003

(65) Prior Publication Data

US 2004/0063732 A1 Apr. 1, 2004

Related U.S. Application Data

(63) Continuation of application No. PCT/FR01/04051, filed on Dec. 19, 2001.

(30) Foreign Application Priority Data

Dec. 26, 2000 (FR) .................................. 00 17009

(51) Int. Cl.
C07D 473/40 (2006.01)
C07D 473/16 (2006.01)
A61P 31/00 (2006.01)
A61K 31/52 (2006.01)

(52) U.S. Cl. .................................. 544/277; 514/263.4
(58) Field of Classification Search ................ 544/277
See application file for complete search history.

(56) References Cited

U.S. PATENT DOCUMENTS

| 5,866,702 A | * | 2/1999 | Mackman et al. ........... 544/277 |
| 6,413,754 B1 |   | 7/2002 | Fay et al. |
| 6,413,975 B1 | * | 7/2002 | Chasin et al. ............... 544/277 |
| 6,479,487 B1 | * | 11/2002 | Dumont et al. ............. 544/277 |
| 6,667,311 B1 | * | 12/2003 | Trova ........................ 544/277 |
| 6,812,232 B1 | * | 11/2004 | Trova ........................ 544/277 |

FOREIGN PATENT DOCUMENTS

| WO | WO 97/16452 | 5/1997 |
| WO | WO 97/20842 | 6/1997 |
| WO | WO 98/05335 | 2/1998 |
| WO | WO 99/07705 | 2/1999 |
| WO | WO 99/07836 | 2/1999 |
| WO | WO 00/49018 | 8/2000 |

OTHER PUBLICATIONS

Kozima S et al., Formation of Organotin-Nitrogen Bonds III*, N-Trialkyltin-5-Substituted Tetrazoles, J. Organometallic Chemistry, vol. 33, 1971, pp 337-346.

* cited by examiner

Primary Examiner—Mark L. Berch
(74) Attorney, Agent, or Firm—Irving Newman

(57) ABSTRACT

The use of purine derivatives of formula (I):

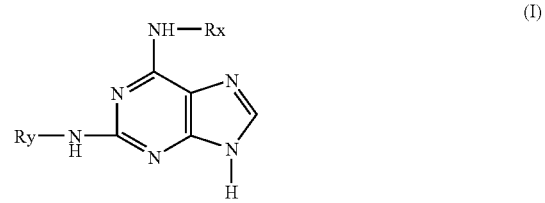

in which:
Rx is —$(Z)_n$—$R_1$ wherein
  Z is a divalent radical selected from —$CH_2$—, —$SO_2$—, —CO—, —COO—, —CONH— and —$(CH_2)_2$—$NR_6$—,
  n is the an integer selected from 0 and 1,
  $R_1$ is selected from hydrogen, aryl, —$CH_2$-aryl, —$SO_2$-aryl, heterocyclic, —$CH_2$-heterocyclic, alkyl and —$SO_2$-alkyl,
Ry is a phenyl radical (optionally substituted) or the radical:

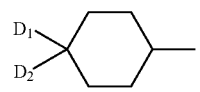

wherein $D_1$ and $D_2$, which are identical or different are selected from hydrogen, hydroxyl, the linear or branched alkyl or alkoxy radicals containing at most 6 carbon atoms and $NHR_5$, or, alternatively, taken together, $D_1$ and $D_2$ form a radical selected from =O and =N—$OR_4$,
$R_4$ is hydrogen, alkyl, aminoalkyl, alkylaminoalkyl, dialkylaminoalkyl, cycloalkyl or aryl,
$R_5$ is hydrogen, alkyl, cycloalkyl, or —COOtBu (Boc), and
$R_6$ is hydrogen, alkyl or cycloalkyl, wherein the alkyl moiety contains 1 to 6, optionally substituted, carbon atoms;
as cdk kinase inhibitors for the prevention and treatment of fungal infections. Also disclosed are novel methods and intermediates for the production of compounds of formula I, as well as pharmaceutical compositions containing said compounds.

3 Claims, No Drawings

PURINE DERIVATIVES, PREPARATION METHOD AND USE AS MEDICINES

CROSS-REFERENCE TO RELATED APPLICATIONS

This application is a continuation of PCT/FR01/04051, filed Dec. 19, 2001, which claims priority from French Patent Application No. 00/17009, filed Dec. 26, 2000.

SUMMARY OF THE INVENTION

The present invention relates to novel purine derivatives, their method of preparation, the novel intermediates obtained, their application as medicines, the pharmaceutical compositions containing them and the novel use of such purine derivatives. The subject of the invention is thus novel purine derivatives.

The products of the present invention may, in particular, possess protein kinase inhibiting properties. Such protein kinases may have particular characteristics. The products of the present invention may thus be endowed with an inhibitory effect toward kinases which activate cyclin-dependent protein kinases called "cdk".

BACKGROUND OF THE INVENTION

The study of the molecular mechanisms which control the cell cycle has made it possible to demonstrate the role of the cdk's thus defined: these cdk's are essential regulators of the cell division cycle; cdk's are proteins which consist of at least two subunits, a catalytic subunit (of which cdc2 is the prototype) and a regulatory subunit each of which is involved in a phase of the cell cycle.

Numerous documents in the literature describe the existence and the role of cdk's and, by way of example, there may be mentioned in particular the document WO 97/20842.

Several kinase inhibitors have been described, such as butyrolactone, flavopiridol and 2(2-hydroxyethylamino)-6-benzylamino-9-methylpurine called olomoucine).

Such cdk activating protein kinases are in particular those of pathogenic fungi which cause infectious diseases in the human body.

As pathogenic fungi, in the context of the present invention, there may be mentioned *Candida albicans* but for example and equally well: *Candida stellatoidea, Candida tropicalis, Candida parapsilosis, Candida krusei, Candida pseudotropicalis, Candida quillermondii, Candida glabrata, Candida lusianiae* or *Candida rugosa* or alternatively mycetes of the *Saccharomyces cerevisiae* type, of the Aspergillus or Cryptococcus type and in particular, for example, *Aspergillus fumigatus, Coccidioides immitis, Cryptococcus neoformans, Histoplasma capsulatum, Blastomyces dermatitidis, Paracoc-cidioides brasiliens* and *Sporothrix schenckii* or alternatively mycetes of the phycomycetes or eumycetes classes, in particular the basidiomycetes, ascomycetes, mehiascomycetales (yeast) and plectascales, and gymnascales (fungus of the skin and of the hair) subclasses, or of the hyphomycetes class, in particular the conidiosporales and thallosporales subclasses among which are the following species: *mucor, rhizopus, coccidioides, paracoccidioides (blastomyces, brasiliensis), endomyces (blastomyces), aspergillus, menicilium (scopulari-opsis), trichophyton, epidermophton, microsporon, piedraia, hormodendron, phialophora, sporotrichon, cryptococcus, candida, geotrichum, trichosporon or toropsulosis, pityriasis Versicolor* or *Erythrasma*.

Among such pathogenic fungi, there may be mentioned most particularly *Candida albicans*. It can be noted that the first kinases activating fungal cdk's were identified in *Saccharomyces cerevisiae* and *Schizosaccharomyces pombe*. The activation of cdk's requires both the attachment of a cyclin molecule and the cdk phosphorylation on a conserved threonine residue located in a region called "T loop". It has been shown that this phosphorylation is carried out by a kinase called "cdk activating kinase" or "CAK". By way of additional information on these "CAK's", there may be mentioned the contents of the documents whose references are as follows:

'Solomon, Trends Biochem. Sci. 19, 496–500 (1994)
'Buck et al, EMBO J., 14(24), 6173–83 (1995)
'Damagnez et al, EMBO J., 14(24), 6164–72 (1995).

In the yeast *Saccharomyces cerevisiae,* a kinase has been identified which is responsible for the CAK activity, which has been called CIV1.

By way of additional information on these "CIV1's", there may be mentioned the contents of the documents whose references are as follows:

Thuret et al, Cell, 86(4), 1996)
Kaldis et al, Cell, 86(4), 553–564 (1996),
Espinosa et al, Science, 273(5282), 1714–1717 (1996).

Such a CAK activity, as defined above, which is essential for survival and cell division, has been found and identified in pathogenic fungi such as, in particular, *Candida albicans:* the sequence of the gene encoding this CIV1 protein in *Candida albicans* called CaCIV1 and the protein CaCIV1 have been identified. Such a sequence and its protein are clearly defined in French Patent Application No. 9710287.

DETAILED DESCRIPTION OF THE INVENTION

There have now, and that is the subject of the present invention, been found products of formula (I) as defined below which may possess properties inhibiting fungal CIV1 protein kinases, these protein kinases activating cdk's.

Thus the present invention relates to products of formula (I) as defined below which may possess in particular inhibitory properties for such a CIV1 protein,which may be found in various fungi as defined above.

The present invention thus relates in particular to products of formula (I) as defined below which may possess more particularly inhibitory properties for *Candida albicans* CaCIV1 protein kinase as defined above and described in French Patent Application No. 9710287.

Such inhibitors of a CIV1 protein which is essential for the cellular survival of yeasts may be used as antifungal agents, either as medicines or industrially.

Their inhibitory properties thus make it possible to use the products of the present invention as fungicides for treating diseases caused by such pathogenic fungi.

Such fungicides are also the subject of the present invention.

Products of the present invention may thus in particular be used as *Candida albicans* fungicides.

The spectrum of fungicidal infections which are known extends from fungal attack on the skin or the nails to more serious mycotic infections of the internal organs. Such infections and diseases which result therefrom are identified as mycoses. Antimycotic substances with fungistatic or fungicidal effects are used for the treatment of these mycoses.

The present invention also relates to the method for preparing such inhibitors, to their use as antifungal agents and to pharmaceutical compositions containing such inhibitors.

The subject of the present invention is the use of products of formula (I):

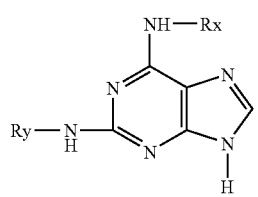

(I)

in which:
Rx represents $-(Z)_n-R_1$ with
Z represents the divalent radical $-CH_2-$, $-SO_2-$, $-CO-$, $-COO-$, $-CONH-$ or $-(CH_2)_2-NR_6-$,
n represents the integer 0 or 1,
$R_1$ is chosen from a hydrogen atom, the aryl, $-CH_2$-aryl, $-SO_2$-aryl, heterocyclic, $-CH_2$-heterocyclic, alkyl and $-SO_2$-alkyl radicals,
Ry represents the optionally substituted phenyl radical or the radical:

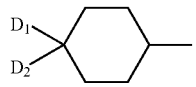

with $D_1$ and $D_2$ either, which are identical or different, are chosen from the hydrogen atom, the hydroxyl radical, the linear or branched alkyl or alkoxy radicals containing at most 6 carbon atoms and the radicals $NHR_5$, or form together the radical $=O$ or $=N-OR_4$,
$R_4$ represents a hydrogen atom, an alkyl, aminoalkyl, alkylaminoalkyl, dialkylaminoalkyl, cycloalkyl or aryl radical,
$R_5$ represents a hydrogen atom, an alkyl or cycloalkyl radical, or the radical $-COOtBu$ (Boc),
$R_6$ represents a hydrogen atom or an alkyl or cycloalkyl radical containing at most 6 optionally substituted carbon atoms,
all the cycloalkyl radicals defined above containing at most 6 carbon atoms,
all the alkyl radicals defined above being linear or branched, containing at most 6 carbon atoms (unless specified),
all the cycloalkyl, alkyl, aryl, phenyl and heterocyclic radicals defined above being optionally substituted with one or more radicals chosen from halogen atoms, hydroxyl, cyano, nitro, trifluoromethyl, trifluoromethoxy and alkoxy radicals containing at most 6 carbon atoms, the radicals with an acid functional group and acid isosteres and the radicals $-NHR_4$, $NR_4R_4'$, $-COR_4$, $-COOR_4$ and $-CONHR_4$ in which $R_4$ has the meaning indicated above and $R_4'$, which is identical to or different from $R_4$, is chosen from the values of $R_4$,
all the aryl and heterocyclic radicals defined above being furthermore optionally substituted with one or more alkyl and phenylalkyl radicals in which the alkyl radicals contain at most 6 carbon atoms,
all the aryl radicals defined above being furthermore optionally substituted with a dioxol radical,
said products of formula (I) being in all the possible isomeric forms, the racemic, enantiomeric and diastereoisomeric forms, and the pharmaceutically acceptable addition salts with inorganic and organic acids or with inorganic and organic bases of said products of formula (I), for the preparation of medicines intended for the prevention or treatment of fungal diseases.

The subject of the present invention is thus the use as defined above of the products of formula (I):

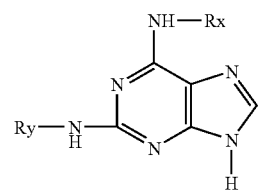

(I)

in which:
Rx represents $-(Z)n-R_1$ with
Z represents the divalent radical $-CH_2-$, $-SO_2-$, $-CO-$, $-COO-$, $-CONH-$ or $-(CH_2)_2-NR_6-$,
n represents the integer 0 or 1,
$R_1$ is chosen from a hydrogen atom, the aryl, $-CH_2$-aryl, $-SO_2$-aryl, heterocyclic, $-CH_2$-heterocyclic, alkyl and $-SO_2$-alkyl radicals,
Ry represents the radical:

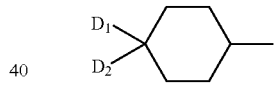

with $D_1$ and $D_2$ either, which are identical or different, are chosen from a hydrogen atom, the hydroxyl radical, the linear or branched alkyl or alkoxy radicals containing at most 6 carbon atoms and the radicals $NHR_5$, or form together the radical $=O$ or $=N-OR_4$,
$R_4$ represents a hydrogen atom, an alkyl, aminoalkyl, cycloalkyl or aryl,
$R_5$ represents a hydrogen atom, an alkyl or cycloalkyl radical, or the radical $-COOtBu$ (Boc),
$R_6$ represents a hydrogen atom or an alkyl or cycloalkyl radical containing at most 6 optionally substituted carbon atoms,
all the cycloalkyl radicals defined above containing at most 6 carbon atoms,
all the alkyl radicals defined above being linear or branched, containing at most 6 carbon atoms (unless specified),
all the cycloalkyl, alkyl, aryl and heterocyclic radicals defined above being optionally substituted with one or more radicals chosen from halogen atoms, hydroxyl, cyano, trifluoromethyl, trifluoromethoxy and alkoxy radicals containing at most 6 carbon atoms, the radicals $-NHR_4$, $-COR_4$, $-COOR_4$ and $-CONHR_4$ in which $R_4$ has the meaning indicated above and the radicals with an acid functional group and acid isosteres, all the aryl and heterocyclic radicals defined above being furthermore optionally substituted with one or more alkyl and phenylalkyl radicals in which the alkyl radicals contain at most 6 carbon atoms, all the aryl radicals defined above being furthermore optionally substituted with a dioxol radical, said products of formula (I) being in all the possible isomeric forms, the racemic, enantiomeric and diastereoisomeric forms, and the additional salts with inorganic and organic acids or with inorganic and organic bases of said products of formula (I).

In the products of formula (I) and in the text which follows:

the term linear or branched alkyl radical denotes methyl, ethyl, propyl, isopropyl, butyl, isobutyl, sec-butyl, tert-butyl, pentyl, isopentyl, hexyl, isohexyl and also heptyl, octyl, nonyl and decyl radicals and their linear or branched position isomers, the term linear or branched alkoxy radical denotes methoxy, ethoxy, propoxy, isopropoxy, linear, secondary or tertiary butoxy, pentoxy or hexoxy and their linear or branched position isomers, the term halogen atom preferably denotes a chlorine atom, but may also represent a fluorine, bromine or iodine atom, the term cycloalkyl radical denotes cyclopropyl and cyclobutyl radicals, and most particularly cyclopentyl and cyclohexyl radicals, the term aryl radical denotes unsaturated, monocyclic radicals or radicals consisting of fused, carbocyclic rings. As examples of such an aryl radical, the phenyl or naphthyl radicals may be mentioned.

the term heterocyclic radical denotes a saturated or unsaturated radical consisting of at most 6 members such that one or more of the members represents an oxygen, sulfur or nitrogen atom: such a heterocyclic radical thus denotes a carbocyclic radical interrupted by one or more heteroatoms chosen from oxygen, nitrogen or sulfur atoms, it being understood that the heterocyclic radicals may contain one or more heteroatoms chosen from oxygen, nitrogen or sulfur atoms and that when these heterocyclic radicals contain more than one heteroatom, the heteroatoms of these heterocyclic radicals may be identical or different. There may be mentioned in particular the radical dioxolane, dioxane, dithiolane, thiooxolane, thiooxane, piperazinyl, piperazinyl substituted with a linear or branched alkyl radical containing at most 4 carbon atoms, thienyl such as 2-thienyl and 3-thienyl, furyl such as 2-furyl, pyridyl such as 2-pyridyl, 3-pyridyl and 4-pyridyl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; it is also possible to mention fused heterocyclic groups containing at least one heteroatom chosen from sulfur, nitrogen and oxygen, for example benzothienyl such as 3-benzothienyl, benzofuryl, benzopyrrolyl, benzimidazolyl, benzoxazolyl, thionaphthyl, indolyl or purinyl. It is also possible to mention most particularly thienyl radicals such as 2-thienyl and 3-thienyl, furyl such as 2-furyl, tetra-hydrofuryl, thienyl, tetrahydrothienyl, pyrrolyl, pyrrolinyl and pyrrolidinyl.

the term acid functional group or acid isostere denotes the free, salified or esterified carboxyl radical, the free or salified tetrazolyl radical, or the radicals:

—$SO_3H$, —$PO(OH)_2$, $NH\,SO_2$—$CF_3$, —NH—$SO_2$—NH—V, NH—$SO_2$—NH—CO—V, NH—CO—V, —NH—CO—NH—V, —NH—CO—NH—$SO_2$—V, —$SO_2$—NH—, —$SO_2$—NH—CO—V, —$SO_2$—NH—CO—NH—V, —CO NH—V, —CO—NH—OH, and —CO—NH—$SO_2$—V in which V represents a linear or branched alkyl or alkenyl radical containing at most 6 carbon atoms or a phenyl radical, these alkyl, alkenyl and phenyl radicals which V represents being optionally substituted with the substituents indicated above for the alkyl and phenyl radicals of the products of formula (I).

The carboxyl radical(s) of the products of formula (I) may be salified or esterified with various groups known to a person skilled in the art among which there may be mentioned, for example:

among the salification compounds, inorganic bases such as, for example, one equivalent of sodium, potassium, lithium, calcium, magnesium or ammonium or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine, N-methylglucamine, among the esterification compounds, alkyl radicals in order to form alkoxycarbonyl groups such as, for example, methoxycarbonyl, ethoxycarbonyl, tert-butoxycarbonyl or benzyloxycarbonyl, it being possible for these alkyl radicals to be substituted with radicals chosen, for example, from halogen atoms, hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

The addition salts with inorganic or organic acids of the products of formula (I) may be, for example, the salts formed with hydrochloric, hydrobromic, hydriodic, nitric, sulfuric, phosphoric, propionic, acetic, trifluoroacetic, formic, benzoic, maleic, fumaric, succinic, tartaric, citric, oxalic, glyoxylic, aspartic and ascorbic acids, alkylmonosulfonic acids such as, for example, methanesulfonic acid, ethanesulfonic acid, propanesulfonic acid, alkyldisulfonic acids such as, for example, methanedisulfonic acid, alpha, beta-ethanedisulfonic acid, arylmonosulfonic acids such as benzenesulfonic acid and aryldisulfonic acids.

It should be recalled that the stereoisomerism may be defined in its broad sense as the isomerism of compounds having the same structural formulae, but in which the various groups are arranged differently in space, such as in particular in monosubstituted cyclohexanes in which the substituents may be in an axial or equatorial position, and the different possible rotational conformations of the ethane derivatives. However, another type of stereoisomerism exists due to the different spatial arrangements of substituents attached either to double bonds or to rings, which is often called geometric isomerism or cis-trans isomerism. The term stereoisomers is used in the present application in its broadest sense and therefore relates to all the compounds indicated above.

The subject of the present invention is particularly the use, as defined above, of the products of formula (I) as defined above which correspond to formula (Ia):

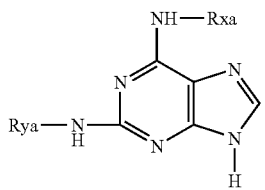

(Ia)

in which:
Rxa represents —(Za)$_n$—R$_1$a with
Za represents the divalent radical —CH$_2$—, —SO$_2$—, —CO— or —(CH$_2$)$_2$—NR$_6$a-,
n represents the integer 0 or 1,
R$_1$a is chosen from a hydrogen atom and the phenyl, —CH$_2$-phenyl, —SO$_2$-phenyl, pyridyl, —CH$_2$-pyridyl, alkyl, —SO$_2$-alkyl and piperidinyl radicals,
Rya represents the optionally substituted phenyl radical or the radical:

with D$_1$a and D$_2$a either, which are identical or different, are chosen from a hydrogen atom, the hydroxyl radical, the linear or branched alkyl and alkoxy radicals containing at most 6 carbon atoms and the NHR$_5$a radicals, or form together the radical =O or =N—OR$_4$a,
R$_4$a represents a hydrogen atom, an alkyl, aminoalkyl, alkylaminoalkyl, dialkylaminoalkyl, cycloalkyl or phenyl radical,
R$_5$a represents a hydrogen atom, an alkyl or cycloalkyl radical or the radical —COOtBu (Boc),
R$_6$a represents a hydrogen atom, an alkyl radical containing at most 4 carbon atoms or a cycloalkyl radical containing at most 6 optionally substituted carbon atoms,
all the cycloalkyl radicals defined above containing at most 6 carbon atoms,
all the alkyl radicals defined above being linear or branched containing at most 6 carbon atoms,
all the cycloalkyl, alkyl, phenyl and piperidinyl radicals defined above being optionally substituted with one or more radicals chosen from halogen atoms and the radicals hydroxyl, cyano, nitro, trifluoromethyl, trifluoromethoxy, alkoxy containing at most 6 carbon atoms, —NHR$_4$a, NR$_4$aR$_4$a', —COR$_4$a, —COOR$_4$a and —CONHR$_4$a in which R$_4$a has the meaning indicated above, and R$_4$a', which is identical to or different from R$_4$a, is chosen from the values of R$_4$a, and the radicals SO$_3$H, PO(OH)$_2$, NH—SO$_2$—CF$_3$, NH—SO$_2$—NH—V and NH—SO$_2$—NH—CO—V in which V represents a phenyl, alkyl or alkenyl radical, the alkyl and alkenyl radicals being linear or branched, containing at most 6 carbon atoms,
all the phenyl and piperidinyl radicals defined above being furthermore optionally substituted with one or more radicals chosen from the alkyl and phenylalkyl radicals in which the alkyl radicals contain at most 6 carbon atoms,
the phenyl radicals defined above being furthermore optionally substituted with a dioxol radical,
said products of formula (Ia) being in all the possible isomeric forms, the racemic, enantiomeric and diastereoisomeric forms, and the addition salts with inorganic and organic acids or with inorganic and organic bases of said products of formula (Ia).

The subject of the present invention is more particularly the use, as defined above, of the products of formula (I) as defined above which correspond to formula (Ib):

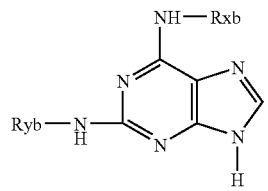

(Ib)

in which:
Rxb represents —(Zb)$_n$—R$_1$b with
Zb represents the divalent radical —CH$_2$—, —SO$_2$—, —CO— or —(CH$_2$)$_2$—NR$_6$b-,
n represents the integer 0 or 1,
R$_1$b is chosen from a hydrogen atom and the phenyl, —CH$_2$-phenyl, —SO$_2$-phenyl, pyridyl, —CH$_2$-pyridyl, alkyl, —SO$_2$-alkyl and piperidinyl radicals, in which the alkyl radical contains at most 4 carbon atoms and the alkyl and phenyl and piperidinyl radicals are optionally substituted as indicated below,
Ryb represents the optionally substituted phenyl radical or the radical:

with D$_1$b and D$_2$b either, which are identical or different, are chosen from a hydrogen atom, the hydroxyl radical, the linear or branched alkyl and alkoxy radicals containing at most 4 carbon atoms and the radicals NHR$_5$b, or form together the radical =O or =N—OR$_4$b,
R$_4$b represents a hydrogen atom, a radical alkyl, aminoalkyl, alkylaminoalkyl, dialkylaminoalkyl in which the alkyl radicals contain at most 4 carbon atoms, phenyl, —CH$_2$-phenyl or the cycloalkyl radical containing at most 6 carbon atoms optionally substituted with the radical —NHR$_6$b,
R$_5$b represents a hydrogen atom, an alkyl or cycloalkyl radical containing at most 6 carbon atoms or the radical —COOtBu (Boc),
R$_6$b represents a hydrogen atom, a radical alkyl containing at most 4 carbon atoms, cycloalkyl containing at most 6 carbon atoms or —CH$_2$-phenyl,
all the cycloalkyl, alkyl, phenyl and piperidinyl radicals defined above being optionally substituted with one or more radicals chosen from halogen atoms and the radicals hydroxyl, cyano, trifluoromethyl, trifluoromethoxy, alkoxy containing at most 4 carbon atoms, free, salified or esterified carboxyl, —NHR$_4$b, NR$_4$bR$_4$b', —COR$_4$b and —CONHR$_4$b in which R$_4$b has the meaning indicated above and R$_4$b', which is identical to or different from R$_4$b, is chosen from the values of R$_4$b, and the radicals SO$_3$H, PO(OH)$_2$ and NH—SO$_2$—CF$_3$, all the phenyl and piperidinyl radicals defined above being furthermore optionally substituted with one or more radicals chosen from alkyl and phenylalkyl radicals in which the alkyl radicals contain at most 4 carbon atoms, the phenyl radicals defined above being furthermore optionally substituted with a dioxol radical, said products of formula (Ib) being in all the possible isomeric forms, the racemic, enantiomeric and diastereoisomeric forms, and the addition salts with inorganic and organic acids or with inorganic and organic bases of said products of formula (Ib).

The subject of the present invention is more particularly the use, as defined above, of the products of formula (I) as defined above which correspond to formula (Ic):

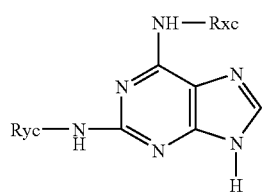

(Ic)

in which:

Rxc represents —(Zc)$_n$—R$_1$c with

Zc represents the divalent radical —CH$_2$—, —SO$_2$—, —CO—, —(CH$_2$)$_2$—NH—, —(CH$_2$)$_2$-Nalkyl, —(CH$_2$)$_2$ $_{N—CH_2}$-phenyl in which the phenyl radicals are optionally substituted with a halogen atom, a radical hydroxyl, trifluoromethyl, alkoxy containing at most 4 carbon atoms or free, salified or esterified carboxyl, n represents the integer 0 or 1, R$_1$c is chosen from a hydrogen atom and the radicals phenyl, —CH$_2$-phenyl, —SO$_2$-phenyl, pyridyl, alkyl, —SO$_2$-alkyl, and piperidinyl optionally substituted on the nitrogen atom with a radical alkyl, phenylalkyl or carboxyl esterified with an alkyl radical, it being understood that in these radicals, all the alkyl radicals are linear or branched, contain at most 4 carbon atoms and are optionally substituted with a free, salified or esterified carboxyl radical, and all the phenyl radicals are optionally substituted with one or more radicals chosen from halogen atoms and the radicals hydroxyl, cyano, trifluoromethyl, nitro, trifluoromethoxy, alkyl and alkoxy containing at most 4 carbon atoms, dioxol, free, esterified or salified carboxyl, —NHR$_4$c, NR$_4$cR$_4$c' and —CONHR$_4$c in which R$_4$c represents a hydrogen atom, an alkyl radical containing at most 4 carbon atoms or a cyclohexyl radical optionally substituted with an NH$_2$ radical and R$_4$c', which is identical to or different from R$_4$c, is chosen from the values of R$_4$c, Ryc represents either the phenyl radical optionally substituted with a radical chosen from the radicals amino, alkylamino, dialkylamino, nitro and carboxyl which is free, salified or esterified with an alkyl radical containing at most 4 carbon atoms, or the radical:

with D$_1$c and D$_2$c either, which are identical or different, are chosen from a hydrogen atom, the hydroxyl radical, the linear or branched alkyl and alkoxy radicals containing at most 4 carbon atoms and the radicals —NH$_2$, —NH—COOtBu or —NHalkyl in which the linear or branched alkyl radical contains at most 4 carbon atoms, or form together the radical =O or =N—Oalkyl, in which the linear or branched alkyl radical contains at most 4 carbon atoms, said products of formula (Ic) being in all the possible isomeric forms, the racemic, enantiomeric and diastereoisomeric forms, and the addition salts with inorganic and organic acids or with inorganic and organic bases of said products of formula (Ic).

The subject of the present invention is most particularly the use, as defined above, of the products of formula (I) as defined above which correspond to formula (Id):

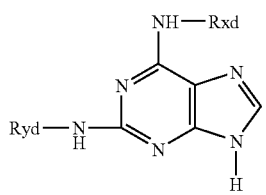

(Id)

in which:

Rxd represents —(Zd)$_n$—R$_1$d with Zd represents a divalent radical —CH$_2$— or —(CH$_2$)$_2$—NH, n represents the integer 0 or 1, R$_1$d is chosen from a hydrogen atom and the radicals phenyl, —CH$_2$-phenyl, pyridyl, alkyl and piperidinyl optionally substituted on the nitrogen atom with a radical alkyl, phenylalkyl or carboxyl esterified with an alkyl radical, it being understood that in all these radicals, the alkyl radicals are linear or branched, contain at most 4 carbon atoms and are optionally substituted with a free, salified or esterified carboxyl radical, and all the phenyl radicals are optionally substituted with one or more radicals chosen from halogen atoms and the radicals hydroxyl, cyano, trifluoromethyl, trifluoromethoxy, alkyl and alkoxy containing at most 4 carbon atoms, dioxol, free, esterified or salified carboxyl, —NHR$_4$c, NR$_4$cR$_4$c' and —CONHR$_4$c in which R$_4$c represents a hydrogen atom, an alkyl radical containing at most 4 carbon atoms or a cyclohexyl radical optionally substituted with an NH$_2$ radical and R$_4$c', which is identical to or different from R$_4$c, is chosen from the values of R$_4$c, Ryd represents either the phenyl radical optionally substituted with a radical chosen from the radicals amino, alkylamino, dialkylamino, nitro and carboxyl which is free, salified or esterified with an alkyl radical containing at most 4 carbon atoms, or the radical:

with D$_1$d, D$_2$d, which are identical or different, are chosen from a hydrogen atom, the hydroxyl radical, the linear or branched alkyl and alkoxy radicals containing at most 4 carbon atoms and the radicals —NH$_2$, —NH—COOtBu or —NHalkyl in which the linear or branched alkyl radical contains at most 4 carbon atoms, or form together the radical =O or =N—Oalkyl, in which the linear or branched alkyl radical contains at most 4 carbon atoms, said products of formula (Id) being in all the possible isomeric forms, the racemic, enantiomeric and diastereoisomeric forms, and the addition salts with inorganic and organic acids or with inorganic and organic bases of said products of formula (Id).

The subject of the present invention is in particular the use, as defined above, of the products of formula (I) as defined in claim 1 which correspond to formula (Ie):

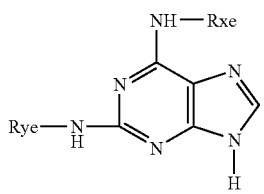

in which:
Rxe represents —(Ze)$_n$—R$_1$e with
Ze represents a divalent radical —CH$_2$— or —(CH$_2$)$_2$—NH,
n represents the integer 0 or 1,
R$_1$e is chosen from a hydrogen atom and the radicals phenyl, —CH$_2$-phenyl, alkyl and piperidinyl optionally substituted on the nitrogen atom with a radical alkyl, carboxyl esterified with an alkyl or a phenylalkyl radical, it being understood that in all these radicals, the phenyl radicals are optionally substituted with one or more radicals chosen from halogen atoms and the radicals hydroxyl, trifluoromethoxy, alkoxy containing at most 4 carbon atoms, amino, alkylamino, dialkylamino, acyl containing at most 4 carbon atoms, and the radicals carboxyl which is free, salified or esterified with an alkyl radical containing at most 4 carbon atoms which is itself optionally substituted with a radical amino, alkylamino, dialkylamino or carboxyl amidated with an amino, alkylamino, dialkylamino or phenylamino radical, Rye represents either the phenyl radical optionally substituted with a radical chosen from the radicals amino, alkylamino, dialkylamino, nitro and carboxyl which is free, salified or esterified with an alkyl radical containing at most 4 carbon atoms, or the radical:

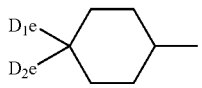

with D$_1$e and D$_2$e represent, one a hydrogen atom, and the other the —NH$_2$ radical optionally substituted with a radical —COOtBu or -alkyl in which the linear or branched alkyl radical contains at most 4 carbon atoms, said products of formula (Ie) being in all the possible isomeric forms, the racemic, enantiomeric and diastereoisomeric forms, and the addition salts with inorganic and organic acids or with inorganic and organic bases of said products of formula (Ie).

The subject of the present invention is particularly the products of formula (I) as defined above which correspond to formula (Ie):

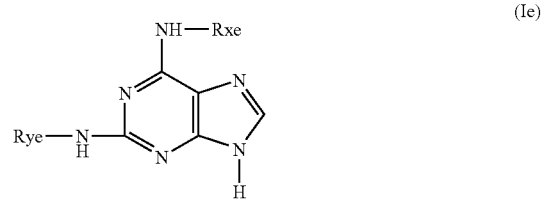

in which:
Rxe represents —(Ze)$_n$—R$_1$e with
Ze represents a divalent radical —CH$_2$— or —(CH$_2$)$_2$—NH,
n represents the integer 0 or 1,
R$_1$e is chosen from a hydrogen atom and the radicals phenyl, —CH$_2$-phenyl, alkyl and piperidinyl optionally substituted on the nitrogen atom with a radical alkyl, carboxyl esterified with an alkyl or a phenylalkyl radical, it being understood that in all these radicals, the phenyl radicals are optionally substituted with one or more radicals chosen from halogen atoms and the radicals hydroxyl, trifluoromethoxy, alkoxy containing at most 4 carbon atoms, and free, esterified or salified carboxyl, Rye represents the radical:

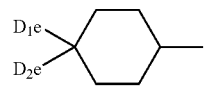

with D$_1$e and D$_2$e represent, one a hydrogen atom, and the other the —NH$_2$ radical optionally substituted with a radical —COOtBu or -alkyl in which the linear or branched alkyl radical contains at most 4 carbon atoms, said products of formula (Ie) being in all the possible isomeric forms, the racemic, enantiomeric and diastereoisomeric forms, and the addition salts with inorganic and organic acids or with inorganic and organic bases of said products of formula (Ie).

In the products of formula (I) as defined above, Rx represents in particular a phenyl radical optionally substituted as indicated above.

The subject of the present invention is most particularly the products of formula (I) as defined above whose names are as follows:

ethyl trans-4-[[2-[(4-aminocyclohexyl)amino]-1H-purin-6-yl]amino]benzoate dihydrochloride trans-N2-(4-aminocyclohexyl)-N6-(2-aminoethyl)-1H-purine-2,6-diamine trihydrochloride trans-N2-(4-aminocyclohexyl)-N6-propyl-1H-purine-2,6-diamine dihydrochloride trans-N2-(4-aminocyclohexyl)-N6-(phenylmethyl)-1H-purine-2,6-diamine dihydrochloride trans-N2-(4-aminocyclohexyl)-N6-(4-methoxyphenyl)-1H-purine-2,6-diamine dihydrochloride trans-N2-(4-aminocyclohexyl)-N6-[4-(trifluoromethoxy)phenyl]-1H-purine-2,6-diamine dihydrochloride trans-N2-(4-aminocyclohexyl)-N6-[1-(phenylmethyl)-4-piperidinyl]-1H-purine-2,6-diamine trihydrochloride
trans-N2-(4-aminocyclohexyl)-N6-[2-[(phenylmethyl)amino]ethyl]-1H-purine-2,6-diamine trihydrochloride
trans-N2-(4-aminocyclohexyl)-N6-[(3,4-dimethoxyphenyl)methyl]-1H-purine-2,6-diamine
trans-N2-(4-aminocyclohexyl)-1H-purine-2,6-diamine dihydrochloride
trans-N2-(4-aminocyclohexyl)-N6-[4-phenyl]-1H-purine-2,6-diamine dihydrochloride
trans-N2-(4-aminocyclohexyl)-N6-(4-fluorophenylmethyl)-1H-purine-2,6-diamine
trans-N2-(4-aminocyclohexyl)-N6-[1-(ethoxycarbonyl)-4-piperidinyl]-1H-purine-2,6-diamine
ethyl trans-3-[[2-[(4-aminocyclohexyl)amino]-9H-purin-6-yl]amino]benzoate
trans-N2-(4-aminocyclohexyl)-N6-(4-chlorophenyl)-9H-purine-2,6-diamine
trans-N2-(4-aminocyclohexyl)-N6-(3,4-dichlorophenyl)-9H-purine-2,6-diamine
butyl trans -4-[[2-[(4-aminocyclohexyl)amino]-9H-purin-6-yl]amino]benzoate
2-(diethylamino)ethyl trans-4-[[2-[(4-aminocyclohexyl)amino]-9H-purin-6-yl]amino]benzoate
trans-4-[[2-[(4-aminocyclohexyl)amino]-9H-purin-6-yl]amino]-N-phenylbenzamide
trans-N2-(4-aminocyclohexyl)-N6-[4-(dimethylamino)phenyl]-9H-purine-2,6-diamine
trans-4-[[2-[(4-aminocyclohexyl)amino]-9H-purin-6-yl]amino]benzaldehyde
trans-4-[[2-[(4-aminocyclohexyl)amino]-9H-purin-6-yl]amino]benzamide
ethyl 4-[[2-[[4-(ethoxycarbonyl)phenyl]amino]-9H-purin-6-yl]amino]benzoate
ethyl 4-[[2-[(3-nitrophenyl)amino]-9H-purin-6-yl]amino]benzoate
ethyl 4-[[2-[(3-aminophenyl)amino]-9H-purin-6-yl]amino]benzoate
ethyl 4-[[2-[[(4-dimethylamino)phenyl]amino]-9H-purin-6-yl]amino]benzoate
ethyl 4-[[2-(cyclohexylamino)-9H-purin-6-yl]amino]benzoate
ethyl 4-[[2-[[3-(ethoxycarbonyl)phenyl]amino]-9H-purin-6-yl]amino]benzoate.

The subject of the present invention is in particular the products of formula (I) as defined above, whose names are as follows:
ethyl trans-4-[[2-[(4-aminocyclohexyl)amino]-1H-purin-6-yl]amino]benzoate dihydrochloride
trans-N2-(4-aminocyclohexyl)-N6-[4-phenyl]-1H-purine-2,6-diamine dihydrochloride
ethyl trans-3-[[2-[(4-aminocyclohexyl)amino]-9H-purin-6-yl]amino]benzoate
trans-N2-(4-aminocyclohexyl)-N6-(3,4-dichlorophenyl)-9H-purine-2,6-diamine
butyl trans-4-[[2-[(4-aminocyclohexyl)amino]-9H-purin-6-yl]amino]benzoate
2-(diethylamino)ethyl trans-4-[[2-[(4-aminocyclohexyl)amino]-9H-purin-6-yl]amino]benzoate
trans-4-[[2-[(4-aminocyclohexyl)amino]-9H-purin-6-yl]amino]-N-phenylbenzamide.

The subject of the present invention is also the method for preparing the products of formula (I), as defined above, characterized in that there is subjected the compound of formula (II):

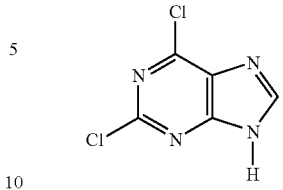

(II)

which is subjected to the reactions of any one of the following routes 1 to 6:

either, according to route 1, the product of formula (II) is subjected to a reaction with a compound of formula (V):

$$NH_2-(Z_1')_n-R_1' \quad (V)$$

in which $R_1'$ has the meaning indicated above for $R_1$, in which the possible reactive functional groups are optionally protected with protecting groups, and n represents the integer 0 or 1 and when n represents 1, then $Z_1'$ represents $-CH_2$ in order to obtain a product of formula (VIII):

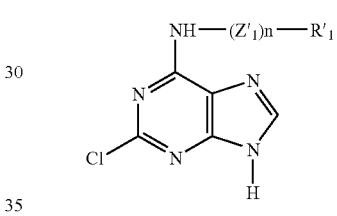

(VIII)

in which $R_1'$ and $Z_1'$ have the meanings indicated above, or, according to route 2, the product of formula (II) is subjected to a reaction with a compound of formula (VI):

$$NH_2-SO_2-R_1' \quad (VI)$$

in which $R_1'$ has the meaning indicated above, in which the possible reactive functional groups are optionally protected with protecting groups, in order to obtain a product of formula (IX):

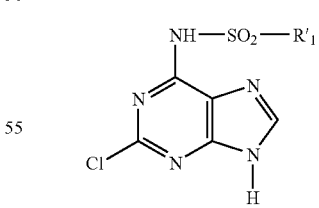

(IX)

in which $R_1'$ has the meaning indicated above, or, according to route 3, the product of formula (II) is subjected to a reaction with the compound of formula (VII):

$$NH_2-(CH_2)_2-NH_2 \quad (VII)$$

in order to obtain a product of formula (X):

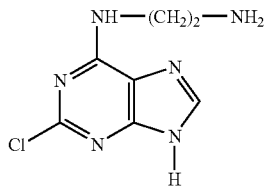
(X)

which product of formula (X) is subjected:

either to a reaction with a compound of formula (XI):

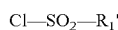 (XI)

in which $R_1'$ has the meaning indicated above, in order to obtain a compound of formula (XII):

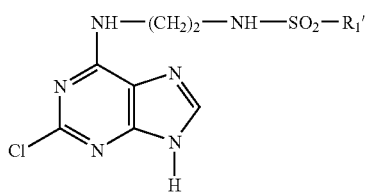 (XII)

in which $R_1'$ has the meaning indicated above, or to a reaction in the presence of a reducing agent with a product of formula (XVII):

 (XVII)

in which $R_7$ represents an aryl, heterocyclic or alkyl radical, these radicals being as defined for the radical $R_1$ above in which the possible reactive functional groups are optionally protected, in order to obtain a product of formula (XIII):

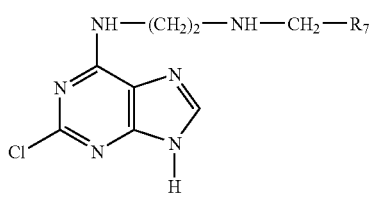 (XIII)

in which $R_7$ has the meaning indicated above, or, according to route 4, the product of formula (II) is subjected to a reaction with a compound of formula (XVIII):

 (XVIII)

in which $R_1'$ has the meaning indicated above, in order to obtain a product

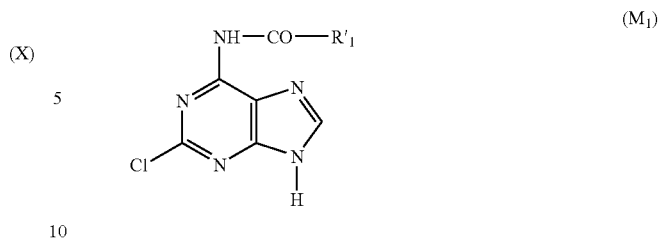 (M₁)

in which $R_1'$ has the meaning indicated above, or, according to route 5 or 6, the product of formula (IV) is subjected to a reaction with ammonia in order to obtain a product of formula ((XIX):

 (XIX)

which product of formula (XIX) is subjected:

either, according to route 5, to a reaction with a product of formula (XX):

 (XX)

in which $R_1'$ has the meaning indicated above, in order to obtain the product of formula (M₂):

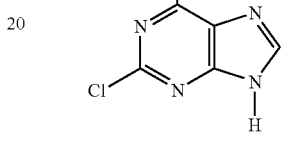 (M₂)

in which $R_1'$ has the meaning indicated above, or, according to route 6, to a reaction with an isocyanate product of formula (XXI):

 (XXI)

in which $R_1'$ has the meaning indicated above, in order to obtain a product of formula (M₃):

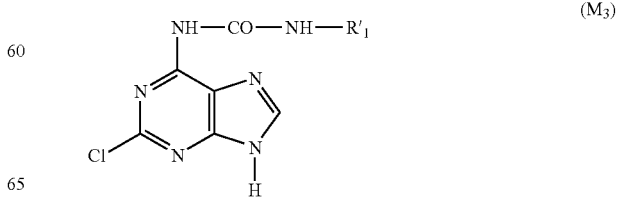 (M₃)

in which $R_1'$ has the meaning indicated above, which products of the formulae (VIII), (IX), (XII), (XIII), $M_1$, $M_2$ and $M_3$ can be subjected to a reaction with a compound of formula (XIV):

(XIV)

in which $D_1'$ and $D_2'$ have the meanings indicated above for $D_1$ and $D_2$, respectively, in which the possible reactive functional groups are optionally protected with protecting groups, in order to obtain a product of formula (I'):

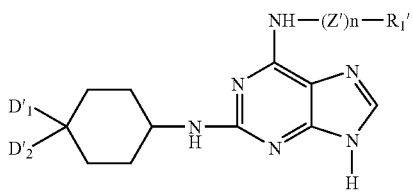
(I')

in which $R_1'$, $D_1'$ and $D_2'$ have the meanings indicated above and Z' has the meaning indicated above for Z in which the possible reactive functional groups are optionally protected with protecting groups, the products of formula (I') having the meaning indicated above for the products of formula (I) in which the possible reactive functional groups are optionally protected with protecting groups, which products of formula (I') may be products of formula (I) and which, in order to obtain products or other products of formula (I), may be subjected, if desired and if necessary, to one or more of the following conversion reactions, in any order:

a) a reaction for esterification of an acid functional group,
b) a reaction for saponification of an ester functional group to an acid functional group,
c) a reaction for oxidation of an alkylthio group to the corresponding sulfoxide or sulfone,
d) a reaction for conversion of a ketone functional group to an oxime functional group,
e) a reaction for reduction of the free or esterified carboxyl functional group to an alcohol functional group,
f) a reaction for conversion of an alkoxy functional group to a hydroxyl functional group, or alternatively of a hydroxyl functional group to an alkoxy functional group,
g) a reaction for oxidation of an alcohol functional group to an aldehyde, acid or ketone functional group,
h) a reaction for conversion of a nitrile radical to a tetrazolyl,
i) a reaction for removal of the protecting groups which may be carried by the protected reactive functional groups,
j) a reaction for salification with an inorganic or organic acid or with a base in order to obtain the corresponding salt,
k) a reaction for resolution of the racemic forms to resolved products, said products of formula (I) thus obtained being in all the possible isomeric forms, the racemic, enantiomeric and stereoisomeric forms.

The subject of the present invention is more precisely the method for preparing the products of formula (I) corresponding to formula (Id) as defined above, characterized in that the compound of formula (II):

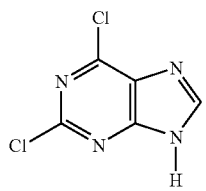
(II)

is subjected to a reaction with a compound of formula (III):

(III)

in which Rxd' has the meaning indicated above for Rxd, in which the possible reactive functional groups are optionally protected with protecting groups, in order to obtain a product of formula (IV):

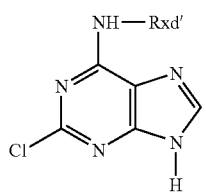
(IV)

in which Rxd' has the meaning indicated above, which products of formula (IV) may be subjected to a reaction with a compound formula (XXII):

(XXII)

in which $D_1'$ and $D_2'$ have the meanings indicated above for $D_1$ and $D_2$, respectively, in which the possible reactive functional groups are optionally protected with protecting groups, in order to obtain a product of formula (I'):

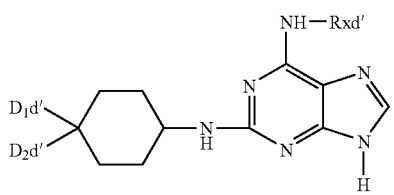
(Id')

in which Rxd', $D_1d'$ and $D_2d'$ have the meanings indicated above, the products of formula (Id') having the meaning indicated above for the products of formula (Id) in which the possible reactive functional groups are optionally protected with protecting groups, which products of formula (Id') may be products of formula (Id) and which, in order to obtain the or other products of formula (Id), may be subjected, if desired and if necessary, to one or more of the following conversion reactions, in any order:

a) a reaction for esterification of an acid functional group,
b) a reaction for saponification of an ester functional group to an acid functional group,
c) a reaction for oxidation of an alkylthio group to the corresponding sulfoxide or sulfone,
d) a reaction for conversion of a ketone functional group to an oxime functional group,
e) a reaction for reduction of the free or esterified carboxyl functional group to an alcohol functional group,
f) a reaction for conversion of an alkoxy functional group to a hydroxyl functional group, or alternatively of a hydroxyl functional group to an alkoxy functional group,
g) a reaction for oxidation of an alcohol functional group to an aldehyde, acid or ketone functional group,
h) a reaction for conversion of a nitrile radical to a tetrazolyl,
i) a reaction for removal of the protecting groups which may be carried by the protected reactive functional groups,
j) a reaction for salification with an inorganic or organic acid or with a base in order to obtain the corresponding salt,
k) a reaction for resolution of the racemic forms to resolved products, said products of formula (Id) thus obtained being in all the possible isomeric forms, the racemic, enantiomeric and stereoisomeric forms.

It may be noted that such reactions for conversion of substituents into other substituents may also be carried out on the starting materials and on the intermediates as defined above before continuing the synthesis according to the reactions indicated in the method described above.

Under preferred conditions for carrying out the invention, the method described above may be carried out in the following manner:

The product of formula (II) is therefore 2,6-dichloropurine which is a commercial product.

The product of formula (II) is subjected, according to route 1) as defined above, to the action of the product of formula (V) as defined above in which n represents the integer 0 and Z represents the radical —$CH_2$— when n is equal to 1, in particular in an alcohol such as butanol at a temperature of about 80° C. or in DMF in order to give a product of formula (VIII) as defined above.

The product of formula (II) is subjected, according to route 2), to the action of the product of formula (VI) as defined above in which Z represents —$SO_2$, in particular in THF, DME in the presence of $Cs_2CO_3$, $K_2CO_3$ or $Na_2CO_3$ in order to give a product of formula (IX) as defined above.

The product of formula (II) is subjected, according to route 3, to the action of the product of formula (VII) as defined above in which Z represents the radical —$(CH_2)_2$ $NR_6$—, in particular in butanol at a temperature of about 75° C. for about 2 or 3 hours in order to give a product of formula (X) as defined above.

The product of formula (X) thus obtained may be subjected of the action of a product of formula (XI) as defined above in DME in the presence of $Cs_2CO_3$ or $CH_2Cl_2$ or $N(Et)_3$ for about one hour at room temperature in order to give a product of formula (XII) as defined above.

The product of formula (X) may also be subjected to the action of an aldehyde of formula (XVII) in particular in in an alcohol such as methanol or ethanol, in the presence of $NaBH_4$ or $NaBH_3CN$ in order to give a product of formula (XIII) as defined above.

For the other values of Z, the corresponding products are prepared according to routes 4, 5 and 6 of the method as follows: the product of formula (II) is subjected according to route 4 to the action of the product of formula (XVIII) in which Z represents CO in order to give a product of formula Ml as defined above.

The reaction of the product of formula (II) with the product of formula XVIII may be carried out under the same conditions as those for the reaction of the product of formula (II) with the product of formula (VI) in order to give the product of formula (IX) in which when Z represents $SO_2$.

The product of the formula (II) is subjected to the action of ammonia in order to give a product of formula XIX. The product of formula XIX may then be subjected either according to route 5 to the action of the product of formula XX in which Z represents COO in order to give a product of formula $M_2$ as defined above, or according to route 6 to the action of the product of formula XXI in which Z represents CONH in order to give a product of formula $M_3$ as defined above.

The reactions of the product of formula XIX with the products of formulae XX or XXI may be carried out in DME or THF, in the presence of $Cs_2CO_3$ or $K_2CO_3$.

The products thus obtained of formulae (VIII), (IX), (XII), (XIII), $M_1$, $M_2$ and $M_3$, as defined above are subjected to the action of a compound of formula (XIV) as defined above, for a condensation reaction which, where appropriate, may be carried out at a temperature of about 140° C.: such a condensation reaction may be followed by a salification reaction in the presence of hydrochloric acid for example or tartaric, citric or methanesulfonic acid, in an alcohol such as for example ethanol or methanol in order to give the products of formula (I') as defined above.

The reaction of the product of formula (II) with a product of formula (III) in order to give a product of formula (IV) as defined above may be carried out in particular in the presence of butanol at a temperature of about 80° C. (from 75 to 85° C. in the examples).

The reaction of the product of formula (IV) thus obtained with a product of formula (XXII) as defined above in order to give a product of formula (Id') as defined above may be carried out in particular with no solvent at a temperature of about 140° C.

The products of formula (Id') as defined above therefore constitute products of formula (I') as defined above.

The amine functional group at the 9-position of the compounds of formula (I') as defined above may be protected with a group such as Boc or $CH_2$-phenyl and may then be released under the customary conditions known to the person skilled in the art.

The saponification reaction may be carried out according to the customary methods known to the person skilled in the art, such as for example in a solvent such as methanol or ethanol, dioxane or dimethoxyethane, in the presence of sodium hydroxide or potassium hydroxide.

The reactions for reduction or oxidation of the product of formula (I') to a product of formula (I) may be carried out according to the customary methods known to a person skilled in the art.

Depending on the values of $R_1'$, $R_3'$, $D_1'$ and $D_2'$, the products of formulae (I') constitute or not products of formula (I) and can give products of formula (I), or may be converted to other products of formula (I) by being subjected to one or more of the reactions a) to k) indicated above.

Thus, the various reactive functional groups which certain compounds in the abovedefined reactions may carry may, if necessary, be protected: they are, for example, hydroxyl, acyl, free carboxyl or amino and monoalkylamino radicals which may be protected with appropriate protecting groups.

The following, nonexhaustive, list of examples of protection for reactive functional groups may be mentioned:

the hydroxyl groups may be protected, for example, with alkyl radicals such as tert-butyl, trimethylsilyl, tert-butyldimethylsilyl, methoxymethyl, tetrahydropyranyl, benzyl or acetyl, the amino groups may be protected, for example, with acetyl, trityl, benzyl, tert-butoxycarbonyl, benzyloxycarbonyl or phthalimido radicals or other radicals known in peptide chemistry, the acyl groups such as the formyl group may be protected, for example, in the form of cyclic or noncyclic ketals or thioketals such as dimethyl or diethyl ketal or ethylenedioxyketal, diethylthioketal or ethylenedithioketal, the acid functional groups of the products described above may be, if desired, amidated with a primary or secondary amine, for example in methylene chloride in the presence, for example, of 1-ethyl-3-(dimethylaminopropyl)carbodiimide hydrochloride at room temperature:

the acid functional groups may be protected, for example, in the form of esters formed with easily cleavable esters such as benzyl or tert-butyl esters or ethers known in peptide chemistry.

The reactions to which the products of formula (I') as defined above may be subjected, if desired or if necessary, may be carried out, for example, as indicated below.

a) The products described above may, if desired, be the subject, on the possible carboxyl functional groups, of esterification reactions which may be carried out according to customary methods known to a person skilled in the art.

b) The possible conversions of ester functional groups to an acid functional group of the products described above may, if desired, be carried out under the customary conditions known to a person skilled in the art, in particular by acid or alkaline hydrolysis, for example with sodium hydroxide or potassium hydroxide, in an alcoholic medium such as, for example, in methanol or with hydrochloric or sulfuric acid.

c) The possible alkylthio groups of the products described above may, if desired, be converted to the corresponding sulfoxide or sulfone functional groups under the customary conditions known to a person skilled in the art such as for example with peracids such as for example peracetic acid or metachloroperbenzoic acid or with oxone, sodium periodate, in solvents such as for example methylene chloride or dioxane at room temperature.

The production of the sulfoxide functional group may be favored by an equimolar mixture of the product containing an alkylthio group and the reagent such as in particular a peracid.

The production of the sulfone functional group may be favored by a mixture of the product containing an alkylthio group with an excess of the reagent such as in particular a peracid.

d) The reaction for conversion of a ketone functional group to an oxime may be carried out under the customary conditions known to the person skilled in the art, such as in particular an action in the presence of an optionally O-substituted hydroxylamine in an alcohol such as for example ethanol, at room temperature or with heating.

e) The possible free or esterified carboxyl functional groups of the products described above may, if desired, be reduced to an alcohol functional group by methods known to the person skilled in the art: the possible esterified carboxyl functional groups may, if desired, be reduced to an alcohol functional group by methods known to the person skilled in the art and in particular with lithium aluminum hydride, in a solvent such as for example tetrahydrofuran or dioxane or ethyl ether.

The possible free carboxyl functional groups of the products described above may, if desired, be reduced to an alcohol functional group in particular with derivatives of boron hydride.

f) The optional alkoxy functional groups such as in particular methoxy functional groups of the products described above may, if desired, be converted to a hydroxyl functional group under the customary conditions known to a person skilled in the art, for example with boron tribromide, in a solvent such as for example methylene chloride, with pyridine hydrobromide or hydrochloride or with hydrobromic or hydrochloric acid, in water or trifluoroacetic acid under reflux.

g) The possible alcohol functional groups of the products described above may, if desired, be converted to an aldehyde or acid functional group by oxidation under the customary conditions known to the person skilled in the art such as, for example, by the action of manganese oxide in order to obtain the aldehydes or of Jones reagent in order to obtain the acids.

h) The possible nitrile functional groups of the products described above may, if desired, be converted to tetrazolyl under customary conditions known to the person skilled in the art such as, for example, by cycloaddition of a metal azide such as for example sodium azide or a trialkyltin azide on the nitrile functional group as is indicated in the method described in the article having the following reference:

J. Organometallic Chemistry, 33, 337 (1971) KOZIMA S. et al.

It may be noted that the reaction for conversion of a carbamate to urea and in particular of a sulfonylcarbamate to sulfonylurea, may be carried out, for example, at the reflux temperature of a solvent such as, for example, toluene, in the presence of a suitable amine.

It is understood that the reactions described above may be carried out as indicated or, where appropriate, according to other customary methods known to the person skilled in the art.

i) The removal of the protecting groups such as, for example, those indicated above may be carried out under the customary conditions known to the person skilled in the art, in particular by acid hydrolysis carried out with an acid such as hydrochloric, benzenesulfonic or para-toluenesulfonic, formic or trifluoroacetic acid or by catalytic hydrogenation.

The phthalimido group may be removed with hydrazine.

A list of the various protecting groups which can be used will be found, for example, in Patent BF 2 499 995.

j) The products described above may, if desired, be the subject of salification reactions, for example, with an inorganic or organic acid or with an inorganic or organic base according to the customary methods known to a person skilled in the art.

k) The possible optically active forms of the product described above may be prepared by resolution of the racemates according to the customary methods known to a person skilled in the art.

Illustrations of such reactions defined above are given in the preparation of the examples described below.

The products of formula (I) as defined above and their addition salts with acids have advantageous pharmacological properties.

The products of the present invention as defined above, possess inhibitory properties for protein kinases as indicated above and in particular for CIV1 as defined above.

The CIV1's play a central role in the entry into the cell cycle by activation of the cdk's, and thus the molecules inhibiting CIV1's are capable of limiting undesirable cell proliferations such as those observed in the growth of fungi.

The products of formula (I) of the present invention may therefore possess antimycotic properties.

These properties justify their application in therapy and the subject of the invention is particularly, as medicines, the products of formula (I) which are defined above, said products of formula (I) being in all the possible isomeric forms, the racemic, enantiomeric and diastereomeric forms, and the pharmaceutically acceptable addition salts with inorganic and organic acids or with inorganic and organic bases of said products of formula (I).

The subject of the invention is more particularly, as medicines, the products as defined for formula (Id) as defined above.

The subject of the invention is most particularly, as medicines, the products described below in the examples and in particular the products of the formula (I) as defined above, which correspond to the following formulae:

ethyl trans-4-[[2-[(4-aminocyclohexyl)amino]-1H-purin-6-yl]amino]benzoate dihydrochloride
trans-N2-(4-aminocyclohexyl)-N6-(2-aminoethyl)-1H-purine-2,6-diamine trihydrochloride
trans-N2-(4-aminocyclohexyl)-N6-propyl-1H-purine-2,6-diamine dihydrochloride
trans-N2-(4-aminocyclohexyl)-N6-(phenylmethyl)-1H-purine-2,6-diamine dihydrochloride
trans-N2-(4-aminocyclohexyl)-N6-(4-methoxyphenyl)-1H-purine-2,6-diamine dihydrochloride
trans-N2-(4-aminocyclohexyl)-N6-[4-(trifluoromethoxy)phenyl]-1H-purine-2,6-diamine dihydrochloride
trans-N2-(4-aminocyclohexyl)-N6-[1-(phenylmethyl)-4-piperidinyl]-1H-purine-2,6-diamine trihydrochloride
trans-N2-(4-aminocyclohexyl)-N6-[2-[(phenylmethyl)amino]ethyl]-1H-purine-2,6-diamine trihydrochloride
trans-N2-(4-aminocyclohexyl)-N6-[(3,4-dimethoxyphenyl)methyl]-1H-purine-2,6-diamine
trans-N2-(4-aminocyclohexyl)-1H-purine-2,6-diamine dihydrochloride
trans-N2-(4-aminocyclohexyl)-N6-[4-phenyl]-1H-purine-2,6-diamine dihydrochloride
trans-N2-(4-aminocyclohexyl)-N6-(4-fluorophenylmethyl)-1H-purine-2,6-diamine
trans-N2-(4-aminocyclohexyl)-N6-[1-(ethoxycarbonyl)-4-piperidinyl]-1H-purine-2,6-diamine
ethyl trans-3-[[2-[(4-aminocyclohexyl)amino]-9H-purin-6-yl]amino]benzoate
trans-N2-(4-aminocyclohexyl)-N6-(4-chlorophenyl)-9H-purine-2,6-diamine
trans-N2-(4-aminocyclohexyl)-N6-(3,4-dichlorophenyl)-9H-purine-2,6-diamine
butyl trans-4-[[2-[(4-aminocyclohexyl)amino]-9H-purin-6-yl]amino]benzoate
2-(diethylamino)ethyl trans-4-[[2-[(4-aminocyclohexyl)amino]-9H-purin-6-yl]amino]benzoate
trans-4-[[2-[(4-aminocyclohexyl)amino]-9H-purin-6-yl]amino]-N-phenylbenzamide
trans-N2-(4-aminocyclohexyl)-N6-[4-(dimethylamino)phenyl]-9H-purine-2,6-diamine
trans-4-[[2-[(4-aminocyclohexyl)amino]-9H-purin-6-yl]amino]benzaldehyde
trans-4-[[2-[(4-aminocyclohexyl)amino]-9H-purin-6-yl]amino]benzamide
ethyl 4-[[2-[[4-(ethoxycarbonyl)phenyl]amino]-9H-purin-6-yl]amino]benzoate
ethyl 4-[[2-[(3-nitrophenyl)amino]-9H-purin-6-yl]amino]benzoate
ethyl 4-[[2-[(3-aminophenyl)amino]-9H-purin-6-yl]amino]benzoate
ethyl 4-[[2-[[(4-dimethylamino)phenyl]amino]-9H-purin-6-yl]amino]benzoate
ethyl 4-[[2-(cyclohexylamino)-9H-purin-6-yl]amino]benzoate
ethyl 4-[[2-[[3-(ethoxycarbonyl)phenyl]amino]-9H-purin-6-yl]amino]benzoate.

The subject of the invention is in particular, as medicines, the products of the formula (I) as defined above, whose names are as follows:

ethyl trans-4-[[2-[(4-aminocyclohexyl)amino]-1H-purin-6-yl]amino]benzoate dihydrochloride
trans-N2-(4-aminocyclohexyl)-N6-[4-phenyl]-1H-purine-2,6-diamine dihydrochloride
ethyl trans-3-[[2-[(4-aminocyclohexyl)amino]-9H-purin-6-yl]amino]benzoate
trans-N2-(4-aminocyclohexyl)-N6-(3,4-dichlorophenyl)-9H-purine-2,6-diamine
butyl trans-4-[[2-[(4-aminocyclohexyl)amino]-9H-purin-6-yl]amino]benzoate
2-(diethylamino)ethyl trans-4-[[2-[(4-aminocyclohexyl)amino]-9H-purin-6-yl]amino]benzoate
trans-4-[[2-[(4-aminocyclohexyl)amino]-9H-purin-6-yl]amino]-N-phenylbenzamide.

The medicines, which are the subject of the invention, find in particular their use in the treatment of diseases due to fungi, such as candidiases, aspergilloses, histoplasmoses and coccidoidoses. The invention extends to pharmaceutical compositions containing, as active ingredient, at least one of the medicines as defined above.

The present invention also relates to a method for screening antifungal products according to the present invention, characterized in that it comprises a step where the activity of a determined protein kinase is measured and then the products having an inhibitory effect on this activity are selected, thus determining the antifungal properties of the products according to the present invention. Such compositions may be useful in particular for treating topical and systemic fungal infections.

The pharmaceutical compositions indicated above may be administered orally, rectally, parenterally or locally as a topical application to the skin and the mucous membranes or by intravenous or intramuscular injection. These compositions may be solid or liquid and may be provided in all the pharmaceutical dosage forms commonly used in human medicine such as, for example, plain or coated tablets, gelatin capsules, granules, suppositories, preparations for injection, ointments, creams, gels, aerosol preparations, pessaries and gynecological capsules. These compositions are prepared according to the customary methods. The active ingredient may be incorporated into excipients normally used in these pharmaceutical compositions, such as talc, gum arabic, lactose, starch, magnesium stearate, cocoa butter, aqueous or nonaqueous vehicles, fatty substances of animal or plant origin, paraffin derivatives, glycols, various wetting agents, dispersants or emulsifiers, preservatives.

The dosage will vary according to the product used, the subject treated and the condition in question, and may be, for example, from 0.05 to 5 g per day in adults, or preferably from 0.1 to 2 g per day.

The subject of the invention is therefore particularly the pharmaceutical compositions as defined above, characterized in that they are used as medicines.

The subject of the invention is thus in particular the use of the products of formula (I) as defined above for the preparation of medicines intended for the prevention or for the treatment of fungal diseases such as mycoses due to fungi chosen in particular from the fungi defined above.

The subject of the invention is more precisely the use of the products of formula (I) as defined above and/or of their pharmaceutically acceptable salts, for the preparation of medicaments intended for the prevention or for the treatment of fungal diseases such as in particular candidiases, aspergilloses, histoplasmoses and coccidoidoses.

The subject of the invention is particularly the use of the products of formula (I) as defined above and/or of their pharmaceutically acceptable salts for the preparation of medicines intended for the prevention or treatment of diseases caused by *Candida albicans*.

The subject of the invention is most particularly the use of the products of formula (I) as defined above and/or of their pharmaceutically acceptable salts for the preparation of medicines intended for the prevention or the treatment of systemic candidiasis.

The subject of the invention is the products of formula (I) as defined above which have antifungal properties as inhibitors of protein kinases CIV1 from *Candida albicans*.

The subject of the invention is thus the pharmaceutical compositions containing, as active ingredient, at least one inhibitor of protein kinases CIV1 from *Candida albicans* as defined above.

The subject of the present invention is in particular the use of the compositions as defined above as antifungal agents.

The starting material of formula (II), that is 2,6-dichloropurine, is known and is commercially available.

Among the starting materials of formulae (III), (V), (VI), (VII), (XI), (XIV) and (XXII), some are known and may be commercially obtained or may be prepared according to the customary methods known to a person skilled in the art.

Among the commercially available starting materials of formulae (III), (V), (VI), (VII), (XI), (XIV) and (XXII), there may be mentioned, for example, the following products:

Among the commercial products of formula (V), there may be mentioned the products methyl 4-(aminomethyl) benzoate hydrochloride, ethyl 4-aminobenzoate, 4-aminobenzamide, methyl 3-aminobenzoate or 3-aminobenzamide.

As commercial products of formula (XIV), there may be mentioned trans-1,4-diaminocyclohexane, trans-4-aminocyclohexanol or benzylamine, para-methoxybenzylamine or para-fluorobenzylamine.

It is also possible in particular to prepare certain starting materials from commercial products, for example by subjecting them to one or more of the reactions described above in a) to k), carried out under the conditions which are also described above.

There may also be mentioned by way of example:

as a product of formula (VI), phenylsulfonamide, 3-bromophenylsulfonamide, 4-tert-butylphenylsulfonamide as a product of formula (VII), ethylenediamine as a product of formula (XI), isopropylsulfonyl chloride, para-methoxyphenylsulfonyl chloride or trifluoromethanesulfonyl chloride as a product of formula (XVII), benzaldehyde, para-methoxybenzaldehyde or para-cyanobenzaldehyde.

The product of formula (III) may be, for example, ethyl 4-aminobenzoate or ethylenediamine: examples of products of formula (II) as defined above are given below in the preparation of the examples of the present invention.

The product of formula (XII) may be in particular diaminocyclohexane.

The experimental part below gives examples of such starting materials.

The subject of the present invention is finally, as novel industrial products, the compounds of formulae (IX), (X), (XII), (XIII), $M_1$, $M_2$ and $M_3$.

The following examples illustrate the invention without however limiting it.

Experimental Part:

EXAMPLE 1

Ethyl trans-4-[[2-[(4-aminocyclohexyl)amino]-1H-purin-6-yl]amino]benzoate dihydrochloride Stage 1: Ethyl 4-[(2-chloro-1H-purin-6-yl)amino]benzoate 945 mg of 2,6-dichloropurine, 5 ml of butanol, 1030 mg of ethyl 4-(amino)benzoate are mixed and the medium is heated at a temperature of 90° C. until complete dissolution is obtained, that is for about 4 hours. The medium is then allowed to return to room temperature, filtered, washed with 20 ml of isopropanol and dried under vacuum at about 75° C.

1550 mg of the expected product are thus obtained in the form of cream-colored crystals.

Stage 2: Ethyl trans-4-[[2-[(4-aminocyclohexyl)amino]-1H-purin-6-yl]amino]benzoate dihydrochloride 970 mg of trans-1,4-diaminocyclohexane are heated to its melting point (70° C.), 269 mg of the product obtained in stage 1 above are added and the medium is then heated at 140–145° C. for 4 hours. The medium is allowed to return to room temperature and it is taken up in 50 ml of a $CH_2Cl_2$-methanol: 80-20 mixture. The medium is washed twice with 20 ml of $H_2O$ and once with 20 ml of sodium chloride as a saturated aqueous solution. The medium is dried over $Na_2SO_4$ and evaporated to dryness.

After purification by chromatography on silica with, as eluent, a mixture of MeOH—$NH_4OH$ (methanol-aqueous ammonia): 98-2.

The medium is crystallized from a mixture of HCl-EtOH (hydrochloric acid-ethanol) at 1.4 N and then it is allowed to cool for 1 hour at room temperature, drained, washed with 5 ml of ethanol and dried under vacuum at about 50° C.

68 mg of the expected product are thus obtained in the form of cream-colored crystals.

Analytical Results: NMR in DMSO (at 60° C.) 1.33 (t) 3H C$\underline{H}_3$—$CH_2$—O—4.32 (q) 2H $CH_3$—C$\underline{H}_2$—O 1.46 (m) 4H axial C$\underline{H}_2$ of cyclohexyl 2.06 (q) 4H equatorial C$\underline{H}_2$ of cyclohexyl 3.05 (bs) 1H axial H4 of the C$\underline{H}$ of cyclohexyl 3.72 (bs) 1H axial H1 of the C$\underline{H}$ of cyclohexyl 8.00 (bs) aromatic 4H 8.17 (bs) 2H–8.52 (bs) 1H H assumed active and CH=N 11.46 active H

EXAMPLE 2

Trans-N2-(4-aminocyclohexyl)-N6-(2-aminoethyl)-1H-purine-2,6-diamine trihydrochloride Stage 1: N-(2-aminoethyl)-2-chloro-1H-purin-6-amine 1200 mg of 2,6-dichloropurine, 12 ml of butanol and 4.2 ml of ethylenediamine (10 eq) are mixed. The medium is heated at a temperature of 75 to 80° C. for about 4 hours 30 minutes. The medium is allowed to return to room temperature, 30 ml of ether are added and then the precipitate obtained is filtered off. It is dissolved under reflux in 90 ml of methanol, the medium is filtered in the hot state, concentrated to 50% and then it is allowed to return to room temperature. The crystals obtained are filtered and then washed with 10 ml of cold methanol.

1020 mg of the expected product are thus obtained in the form of white crystals.

Stage 2: Trans-N2-(4-aminocyclohexyl)-N6-(2-aminoethyl)-1H-purine-2,6-diamine trihydrochloride 303 mg of the product obtained in stage 1 above and 800 mg of 2,4-diaminocyclohexane (7 mmol) are mixed and the medium is heated at the temperature of 140° C. for about 2 hours 30 minutes. 3 to 5 ml of a mixture of MeOH—$CH_2Cl_2$: 50-50 are then added. The medium is filtered, evaporated and taken up in a mixture of $CH_2Cl_2$—MeOH—$NH_4OH$ (dichloromethane-methanol-aqueous ammonia): 4-4-1.

After purification by chromatography on silica with, as eluent, a mixture of $CH_2Cl_2$-MeOH—$NH_4OH$: 4--4-1, the medium is evaporated, crystallized from a mixture of HCl-EtOH (hydrochloric acid-ethanol) at 1.4 N and then allowed to cool for 1 hour at room temperature, drained, washed with 3 ml of ethanol and dried under vacuum at about 50° C.

37 mg of the expected product are thus obtained in the form of beige-colored crystals.

Analytical Results: NMR in DMSO (at 60° C.) 1.39 (m) 2H–1.58 (m) 2H-2.04 (dl) 4H $CH_2$ of cyclohexyl 3.03 (bs) 1H axial H4 of the $CH$ of cyclohexyl 3.81 (bs) 1H axial H1 of the $CH$ of cyclohexyl 3.14 (m) 2H $H_2N$—$CH_2$—$CH_2$—NH 8.23 (bs) 2H $H_2N$—$CH_2$—$CH_2$—NH 3.82 (m) 2H $H_2N$—$CH_2$—$CH_2$—NH 9.54 (bs) 1H $H_2N$—$CH_2$—$CH_2$—$NH$ 8.15 (bs) 2H $NH_2$ on the ring 8.22 (s) H8 N=C$H$ 7.84 to 8.34 (m) 2 active H

EXAMPLE 3

Trans-N2-(4-aminocyclohexyl)-N6-propyl-1H-purine-2,6-diamine dihydrochloride

Stage 1: N-propyl-2-chloro-1H-purin-6-amine 189 mg of 2,6-dichloropurine, 4 ml of butanol and 0.09 ml (1.1 mol) of propylamine are mixed at room temperature and the medium is heated at a temperature of 75° C. for 2 hours 30 minutes.

The medium is allowed to return to room temperature, drained and washed with 5 ml of ether and dried under vacuum at about 50° C.

175 mg of the expected product are thus obtained in the form of beige-colored crystals.

Stage 2 Trans-N2-(4-aminocyclohexyl)-N6-propyl-1H-purine-2,6-diamine dihydrochloride 560 mg of trans-1,4-diaminocyclohexane are heated to its melting point (70° C.), 148 mg of the product obtained in stage 1 above are added and the medium is then heated at about 140° C. for about 5 hours 30 minutes and then allowed to stand overnight at room temperature. After purification by chromatography on silica with, as eluent, a mixture of MeOH—$NH_4OH$: 98-2, the medium is taken up in 4 ml of ethanol, 2 ml of a hydrochloric acid-ethanol 1.4 N mixture are added, about 3 ml of ether are added, and the precipitate is drained, washed with 3 ml of ether and dried under vacuum at about 60° C.

103 mg of the expected product are thus obtained in the form of white crystals.

Analytical Results: NMR in DMSO (at 60° C.) 0.97 (t) 3H $CH_3$—$CH_2$—$CH_2$—NH 1.66 2H $CH_3$—$CH_2$—$CH_2$—NH 3.50 (m) 2H $CH_3$—$CH_2$—$CH_2$—NH in the active H 1.45 (m) 4H-2.05 (m) 4H $CH_2$ of cyclohexyl 3.03 (bs) 1H axial H4 of the $CH$ of cyclohexyl 3.73 (bs) 1H axial H1 of the $CH$ of cyclohexyl 7.86 (bs)–9.43 (bs) 2 active H 8.09 (bs) 3H–8.16 (bs) 1H active H+N=C$H$

EXAMPLE 4

Trans-N2-(4-aminocyclohexyl)-N6-(phenylmethyl)-1H-purine-2,6-diamine dihydrochloride Stage 1: 2-chloro-N-(phenylmethyl)-1H-purin-6-amine 189 mg of 2,6-dichloropurine, 4 ml of butanol and 0.12 ml (1.1 mol) of benzylamine are mixed at room temperature and the medium is heated at a temperature of 75° C. for 5 hours and then it is left at room temperature overnight.

After purification by chromatography on silica with, as eluent, a mixture of $CH_2Cl_2$-MeOH: 90-10, the medium is drained and washed with 5 ml of ether and then dried under vacuum at about 50° C.

258 mg of the expected product are thus obtained in the form of beige-colored crystals.

Stage 2 Trans-N2-(4-aminocyclohexyl)-N6-(phenylmethyl)-1H-purine-2,6-diamine dihydrochloride 560 mg of trans-1,4-diaminocyclohexane are heated to its melting point (70° C.), 182 mg of the product obtained in stage 1 above are added and the medium is then heated at about 140° C. for about 7 hours and then allowed to stand overnight at room temperature. After purification by chromatography on silica with, as eluent, a mixture of MeOH—$NH_4OH$: 98-2, the medium is taken up with 7 ml of ethanol, 4 ml of a hydrochloric acid-ethanol in proportion 1.4 N mixture are added, the medium is left to crystallize and then drained, washed with 3 ml of ethanol and dried under vacuum at about 60° C.

44 mg of the expected product are thus obtained in the form of beige crystals.

Analytical Results: NMR in DMSO (at 60° C.) 1.41 (m) 4H–1.98 (t1) 4H $CH_2$ of cyclohexyl 3.01 (bs) 1H axial H4 of the $CH$ of cyclohexyl 3.70 (bt) 1H axial H1 of the $CH$ of cyclohexyl 4.75 (bs) 2H—N—$CH_2$-phenyl 7.23 to 7.43 (m) 5H aromatic H 7.82 (bs)–9.91 (bs) 2 active H 8.08 (bs) 3H–8.20 (s) 1H active H+N=C$H$

EXAMPLE 5

Trans-N2-(4-aminocyclohexyl)-N6-(4-methoxyphenyl)-1H-purine-2,6-diamine dihydrochloride Stage 1: 2-chloro-N-(4-methoxyphenyl)-1H-purin-6-amine 189 mg of 2,6-dichloropurine, 4 ml of butanol and 135 mg (1.1 mol) of 4-methoxybenzenamine are mixed at room temperature and the medium is heated at a temperature of 75° C. for 5 hours and then left at room temperature overnight.

After purification by chromatography on silica with, as eluent, a mixture of $CH_2Cl_2$-MeOH: 90-10, the medium is drained and washed with 5 ml of ether and then dried under vacuum at about 50° C.

257 mg of the expected product are thus obtained in the form of gray-colored crystals.

Stage 2: Trans-N2-(4-aminocyclohexyl)-N6-(4-methoxyphenyl)-1H-purine-2,6-diamine dihydrochloride 559 mg of trans-1,4-diaminocyclohexane are introduced at room temperature, heated until melting is obtained (70° C.), 193 mg (0.7 mol) of the product obtained in stage 1 above are added and then the medium is left for about 3 hours 30 minutes at 140° C. and then it is allowed to return to room temperature. After purification by chromatography on silica with, as eluent, a mixture of MeOH—$NH_4OH$: 98-2, the medium is taken up with 5 ml of ethanol, 4 ml of a hydrochloric acid-ethanol 1.4 N mixture are added, the medium is left to crystallize and then drained, washed with 3 ml of ethanol and dried under vacuum at about 60° C. 71 mg of the expected product are thus obtained in the form of orange-colored crystals.

Analytical Results: NMR in DMSO (at 60° C.) 1.46 (m) 4H–2.03 (m) 4H C$\underline{H}_2$ of cyclohexyl 3.03 (bs) 1H axial H4 of the C$\underline{H}$ of cyclohexyl 3.70 (bs) 1H axial H1 of the C$\underline{H}$ of cyclohexyl 3.79 (s) 3H C$\underline{H}_3$—O-phenyl 7.01 to 7.82 (m) aromatic H 8.07 (bs) 3H–8.35 (bs) 1H-11.30 (bs) 1H active H+N=C$\underline{H}$

EXAMPLE 6

Trans-N2-(4-aminocyclohexyl)-N6-[4-(trifluoromethoxy)phenyl]-1H-purine-2,6-diamine dihydrochloride Stage 1: 2-chloro-N-[4-(trifluoromethoxy)phenyl]-1H-purin-6-amine 189 mg of 2,6-dichloropurine, 4 ml of butanol and 0.14 ml (1.1 mol) of 4-(trifluoromethoxy)benzeneamine are mixed at room temperature and the medium is heated at a temperature of 75° C. for 2 hours 30 minutes. The medium is allowed to return to room temperature, drained and washed with 5 ml of ether and then dried under vacuum at about 50° C. 130 mg of product are thus obtained: the mother liquors are evaporated to dryness, the medium is taken up with twice 50 ml of a $CH_2Cl_2$—AcOEt: 50-50 mixture, washed with 15 ml of a saturated $NH_4Cl$ solution, dried, filtered and evaporated to dryness. The mixture is then impasted in 5 ml of ether and dried at room temperature.

160 mg of product are thus obtained.

290 mg of the expected product are thus obtained in total in the form of off-white-colored crystals.

Stage 2 Trans-N2-(4-aminocyclohexyl)-N6-[4-(trifluoromethoxy)phenyl]-1H-purine-2,6-diamine dihydrochloride 400 mg of trans-1,4-diaminocyclohexane are introduced at room temperature, heated to about 140° C., 165 mg (0.5 mol) of the product obtained in stage 1 above are added and the medium is kept at 140° C. for about 6 hours and then it is allowed to return to room temperature. After purifying by chromatography on silica with, as eluent, a mixture of MeOH—$NH_4OH$: 98-2, the medium is taken up with 4 ml of ethanol, 2 ml of a hydrochloric acid-ethanol 1.4 N mixture are added, 3 ml of ether are added, and the medium is drained, washed with 2 ml of ether and dried under vacuum at about 60° C.

75 mg of the expected product are thus obtained in the form of white crystals.

Analytical Results: NMR in DMSO (at 60° C.) 1.47 (m) 4H–2.03 (m) 4H C$\underline{H}_2$ of cyclohexyl 3.03 (b) 1H axial H4 of the C$\underline{H}$ of cyclohexyl 3.73 (b) 1H axial H1 of the C$\underline{H}$ of cyclohexyl 7.43 (d) to 8.08 (masked) aromatic H 8.09 (bs)–8.51 (bs)–11.6 (bs) 1H active H+N=C$\underline{H}$

EXAMPLE 7

Trans-N2-(4-aminocyclohexyl)-N6-[1-(phenylmethyl)-4-piperidinyl]-1H-purine-2,6-diamine trihydrochloride Stage 1: 2-chloro-N-[1-(phenylmethyl)-4-piperidinyl]-1H-purin-6-amine 189 mg of 2,6-dichloropurine, 4 ml of butanol and 0.22 ml (1.1 mol) of 1-(phenylmethyl)-4-piperidinamine are mixed at room temperature and the medium is heated at a temperature of 75° C. for 2 hours 30 minutes. After purification by chromatography on silica with, as eluent, a mixture of $CH_2Cl_2$-MeOH: 90-10, the medium is evaporated to dryness and impasted in 10 ml of ether and then dried under vacuum at about 50° C.

474 mg of the expected product are thus obtained in the form of beige-colored crystals.

Stage 2: Trans-N2-(4-aminocyclohexyl)-N6-[1-(phenylmethyl)-4-piperidinyl]-1H-purine-2,6-diamine trihydrochloride 560 mg of trans-1,4-diaminocyclohexane are introduced at room temperature, heated to about 140° C., 240 mg (0.7 mol) of the product obtained in stage 1 above are added and the medium is kept at 140° C. for about 4 hours and then it is allowed to return to room temperature. After purification by chromatography on silica with, as eluent, a mixture of MeOH—NH4OH: 98-2, the medium is taken up with 3 ml of ethanol, 2 ml of a hydrochloric acid-ethanol 1.4 N mixture are added, the medium is evaporated, washed with 2 ml of ether and dried under vacuum at about 60° C.

42 mg of the expected product are thus obtained in the form of an amorphous powder.

Analytical Results: NMR in DMSO (at 60° C.) 1.38 (m); 1.71 (m); 2.02 (m); 2.12 (m); 2.20 (m) C$\underline{H}_2$ of cyclohexyl and —C$\underline{H}_2$—CH— of piperidine 3.08 (m); 3.20 (m); 3.35 (m); 3.52 (bd); 3.70 (bs) C$\underline{H}$ of cyclohexyl and $CH_2$—N of piperidine 4.22 (s); 4.25 (s); 4.42 (bs) N—C$\underline{H}_2$-phenyl and CH of piperidine 7.38 (m) 5 aromatic H 7.86 (s)–7.90 (s) active H+N=C$\underline{H}$

EXAMPLE 8

Trans-N2-(4-aminocyclohexyl)-N6-[2-[(phenylmethyl)amino]ethyl]-1H-purine-2,6-diamine trihydrochloride Stage 1: 2-chloro-N-[2-[(phenylmethyl)amino]ethyl]-1H-purin-6-amine 235 mg of the product obtained in stage 1 of Examples 2, 4 ml of methanol, 2 ml of tetrahydrofuran and then 2 ml of methanol, 0.2 ml of acetic acid and 0.16 ml of benzaldehyde (0.0016 mol) are mixed and the medium is stirred at room temperature for about 16 hours. About 100 mg of NaBH3CN (sodium cyanoborohydride) (0.0016 mol) are then added and the medium is kept stirred for 1 hour. The medium is evaporated, purified by chromatography on silica with, as eluent, $CH_2Cl_2$-MeOH—NH40H (dichloromethane-methanol-aqueous ammonia): 90-10-1.

138 mg of the expected product are thus obtained in the form of an amorphous solid.

Stage 2: Trans-N2-(4-aminocyclohexyl)-N6-[2-[(phenylmethyl)amino]ethyl]-1H-purine-2,6-diamine trihydrochloride 138 mg of the product obtained in stage 1 above and 340 mg of 2,4-diaminocyclohexane (3 mmol) (6.6 eq) are mixed and the medium is heated at the temperature of 140° C. for about 2 hours 30 minutes. The medium is then dissolved in a $CH_2Cl_2$-MeOH—$NH_4OH$: 78-20-2 mixture and purified by chromatography on silica with, as eluent, a mixture of $CH_2Cl_2$-MeOH—$NH_4OH$: 78-20-2. The medium is evaporated, crystallized from a mixture of HCl-EtOH (hydrochloric acid-ethanol) at 1.4 N, drained, washed with 2 ml of ethanol and dried under vacuum at about 50° C.

11 mg of the expected product are thus obtained in the form of an amorphous powder.

Analytical Results: NMR in DMSO (at 60° C.) 1.3 to 1.7 4H–2.04 (m) 4H C$\underline{H}_2$ of cyclohexyl 3.02 (bs) 1H axial H4 of the C$\underline{H}$ of cyclohexyl 3.68 (m)–3.81 (m) 1H axial H1 of the C$\underline{H}$ of cyclohexyl 3.28 (t)–3.95 (b)–3.41–4.09 (t) N—C$\underline{H}_2$—C$\underline{H}_2$—N 4.19 (bs)–4.23(bs) N—C$\underline{H}_2$-phenyl 7.41 (m) 3H–7.54 (m) and 7.61 (m) 2H aromatic H 8.07 (bs) 3H–8.35 (bs) 1H–11.30 (bs) 1H active H+N═C$\underline{H}$8.18–8.01 N═C$\underline{H}$8.06 2H–9.46–9.57 1H active H

EXAMPLE 9

Trans-N2-(4-aminocyclohexyl)-N6-[(3,4-dimethoxyphenyl)methyl]-1H-purine-2,6-diamine Stage 1: 2-chloro-N-[4-(3,4-dimethoxyphenyl)methyl]-1H-purin-6-amine 189 mg of 2,6-dichloropurine, 2 ml of butanol and 209 mg (1.25 eq) of 3,4-dimethoxybenzenemethanamine are mixed and the medium is left overnight at a temperature of 80° C. The medium is then allowed to return to room temperature, filtered, washed with 5 ml of isopropanol and dried under vacuum at about 75° C.

378 mg of the expected product are thus obtained in the form of beige-colored crystals.

Stage 2: Trans-N2-(4-aminocyclohexyl)-N6-[(3,4-dimethoxyphenyl)methyl]-1H-purine-2,6-diamine 570 mg of trans-1,4-diaminocyclohexane are heated to its melting point (70° C.), 160 mg of the product obtained in stage 1 above are added and the medium is kept at 140° C. for 20 hours. The medium is allowed to return to room temperature and is taken up in 2 ml of an MeOH—$NH_4OH$: 98-2 mixture, and then purified by chromatography on silica with, as eluent, a mixture of MeOH—$NH_4OH$: 98-2. A second chromatography is carried out with, as eluent, a $CH_2Cl_2$-MeOH—$NH_4OH$: 75-22-3 mixture.

55 mg of the expected product are thus obtained in the form of a pink-beige crumbly foam.

Analytical Results: NMR in DMSO (at 60° C.) 1.22 (m) 4H–1.89 (m) 4H C$\underline{H}_2$ of cyclohexyl 2.65 (m) 1H axial H4 of the C$\underline{H}$ of cyclohexyl 3.65 (m) 1H axial H1 of the C$\underline{H}$ of cyclohexyl 4.62 (bd) 2H phenyl-C$\underline{H}_2$—NH 7.16 (bt) 1H phenyl-CH$_2$—N$\underline{H}$3.73 (s)–3.74 (s) 6H phenyl-O—C$\underline{H}_3$6.86 (d) 1H–6.91 (dd) 1H–7.05 (d) 1H (3H Ar) aromatic H 7.59 (s) 1H—N═C$\underline{H}$—N 5.58 (bd) 1H N$\underline{H}$ in 1

EXAMPLE 10

Trans-N2-(4-aminocyclohexyl)-1H-purine-2,6-diamine dihydrochloride

Stage 1: 2-chloro-1H-purin-6-amine 567 mg of 2,6-dichloropurine, 12 ml of butanol and 1.5 ml (1.1 mol) of hydroxylamine are mixed at room temperature, the medium is heated at a temperature of 80° C. for about 24 hours and then it is allowed to return to room temperature. After purification by chromatography on silica with, as eluent, a mixture of $CH_2Cl_2$-MeOH: 90-10, the medium is drained and washed with 5 ml of ether and then dried under vacuum at about 50° C.

458 mg of the expected product are thus obtained in the form of an amorphous solid.

Stage 2: Trans-N2-(4-aminocyclohexyl)-1H-purine-2,6-diamine dihydrochloride 1490 mg of trans-1,4-diaminocyclohexane are introduced, heated to about 140° C., 458 mg (12.7 mmol) of the product obtained in stage 1 above are added and the medium is kept at 140° C. for about half an hour. After purification by chromatography on silica with, as eluent, an MeOH—$NH_4OH$: 98-2 mixture, the medium is taken up with 4 ml of ethanol, 4 ml of a hydrochloric acid-ethanol 1.4 N mixture are added, the precipitate is drained, washed with 3 ml of ethanol and dried under vacuum at about 50° C.

77 mg of the expected product are thus obtained in the form of pink-beige-colored crystals.

Analytical Results: NMR in DMSO (at 60° C.) 1.38 (m)–1.98 (m) 8H C$\underline{H}_2$ of cyclohexyl 2.94 (bs) 2H H1 and H4 of the C$\underline{H}$ of cyclohexyl 8.07 (bs) 5 active H+–N═C$\underline{H}$

EXAMPLE 11

Trans-N2-(4-aminocyclohexyl)-N6-[4-phenyl]-1H-purine-2,6-diamine dihydrochloride Stage 1: 2-chloro-N-phenyl-1H-purin-6-amine 189 mg of 2,6-dichloropurine, 4 ml of butanol and 0.1 ml (1.1 mol) of aniline are mixed at room temperature and the medium is heated to a temperature of 80° C. for 2 hours. The medium is then allowed to return to room temperature, it is drained and washed with 5 ml of ether and dried under vacuum at about 50° C.

183 mg of the expected product are thus obtained in the form of colorless crystals.

Stage 2: Trans-N2-(4-aminocyclohexyl)-N6-[4-phenyl]-1H-purine-2,6-diamine dihydrochloride 400 mg of trans-1,4-diaminocyclohexane are heated to its melting point at about 70° C., 123 mg of the product obtained in stage 1 above are added and the medium is then heated to about 140° C. for about 5 hours 30 minutes and then left at room temperature. After purification by chromatography on silica with, as eluent, an MeOH—NH$_4$OH: 98-2 mixture, the medium is taken up in 5 ml of ethanol, 4 ml of a hydrochloric acid-ethanol 1.4 N mixture are added, the medium is evaporated to dryness, impasted with ether and dried under vacuum at about 60° C.

80 mg of the expected product are thus obtained in the form of a brown solid.

Analytical Results: NMR in DMSO (at 60° C.) 1.24(m) –1.41(m)–1.85 (m)–2.08(m): the C$\underline{H}_2$ of cyclohexyl 2.96 (m)–3.04 (m)–3.56 (m)–3.77 (m) the C$\underline{H}$ of cyclohexyl 7.18(t)–7.44 (t)–7.96 (b) aromatic H of -phenyl-NH 8.42 (s) N=C$\underline{H}$—N 8.11 (b)–11.5 active H

EXAMPLE 12

Trans-N2-(4-aminocyclohexyl)-N6-(4-fluorophenyl-methyl)-1H-purine-2,6-diamine

Stage 1: 2-chloro-N-(4-fluorophenylmethyl)-1H-purin-6-amine 189 mg of 2,6-dichloropurine, 2 ml of butanol and 156 mg (1.25 equivalents) of 4-fluorobenzylamine are mixed at room temperature, and the medium is heated at a temperature of 80° C. overnight. The medium is allowed to return to room temperature, 2 ml of isopropanol are added, the medium is drained and washed with 3 ml of isopropanol and then dried under vacuum at about 60° C.

300 mg of the expected product are thus obtained in the form of beige-colored crystals.

Stage 2: Trans-N2-(4-aminocyclohexyl)-N6-(4-fluorophenylmethyl)-1H-purine-2,6-diamine 570 mg of trans-1,4-diaminocyclohexane are heated to its melting point 70° C., 290 mg of the product obtained in stage 1 above are added and the medium is then heated at approximately 140° C. for about 4 hours and then left overnight at room temperature. After purification by chromatography on silica with, as eluent, a mixture of CH$_2$Cl$_2$: MeOH:NH$_4$OH (75:22:3) 93 mg of the expected product are obtained in the form of a beige crumbly foam.

Analytical Results: NMR in DMSO (at 60° C.) 1.21(m) 4H–1.83 (m) 2H–1.91 (m) 2H: the C$\underline{H}_2$ of cyclohexyl 3.60 (masked) 1H–2.65 (m) 1H C$\underline{H}$ of cyclohexyl 4.64 (d) —NH—C$\underline{H}_2$-phenyl-F 7.40 (masked) —N $\underline{H}$—CH$_2$-phenyl-F 7.40 (m)–7.08 (t) aromatic H 7.60 (s) N=C$\underline{H}$—N

EXAMPLE 13

Trans-N2-(4-aminocyclohexyl)-N6-[1-(ethoxycarbonyl)-4-piperidinyl)-1H-purine-2,6-diamine Stage 1: 2-chloro-N-[1-ethoxycarbonyl)-4-piperidinyl]-1H-purin-6-amine The procedure is carried out as in stage 1 of Example 12 by mixing 189 mg of 2,6-dichloropurine, 2 ml of butanol and 215 mg (1.25 equivalents) of ethyl 4-amino-1-piperidine carboxylate and the medium is heated at a temperature of 80° C. for 2 hours 30 minutes. The medium is then evaporated under vacuum. After purification by chromatography on silica with, as eluent, a mixture of CH$_2$Cl$_2$:MeOH: (90:10), 217 mg of the expected product are thus obtained in the form of beige crystals.

Stage 2: Trans-N2-(4-aminocyclohexyl)-N6-[1-(ethoxycarbonyl)-4-piperidinyl]-1H-purine-2,6-diamine 217 mg of the product obtained in stage 1 above and 763 mg of trans-1,4-diaminocyclohexane are mixed and the medium is heated at about 140° C. for about 5 hours and then allowed to return to room temperature. After purification by chromatography on silica with, as eluent, a mixture of MeOH:NH$_4$OH (98:2), 71 mg of the expected product are obtained in the form of a pink-beige crumbly foam.

Analytical Results: NMR in DMSO (at 60° C.) 1.20 (t) 3H C$\underline{H}_3$—CH$_2$—O—C=O 4.06 (q) 2H CH$_3$—C $\underline{H}_2$—O—C=O 2.91 (td)–4.09 (bd) 4H; 1.51 (qd)–1.93 (m)4H; —C$\underline{H}_2$— of piperidine 4.27 (bs) 1H; —C$\underline{H}$— of piperidine 6.58 (bd) 1H —N$\underline{H}$— of piperidine 1.12 (m)–1.27 (m)–1.80 (bd)–1.95 (m) 8H C$\underline{H}_2$ of cyclohexyl 2.56 (tt) 1H H4–3.62(m) 1H H1-NH CH of cyclohexyl 5.52 (bd) 1H H1-N$\underline{H}$7.59 (s) 1H N=C$\underline{H}$—N

EXAMPLE 14

Ethyl trans-3-[[2-[(4-aminocyclohexyl)amino]-9H-purin-6-yl]amino]benzoate

Stage 1: Ethyl 3-[(2-chloro-9H-purin-6-yl]amino]benzoate

The procedure is carried out as in Example 1, starting with 189 mg of 2,6-dichloropurine, 5 ml of butanol and 206 mg of ethyl 3-aminobenzoate. 275 mg of the expected product are thus obtained.

Stage 2: Ethyl trans-3-[[2-[(4-aminocyclohexyl)amino]-9H-purin-6-yl]amino]benzoate 570 mg of trans 1,4-diaminocyclohexane are heated to its melting point (70° C.) and 158 mg of the product obtained in stage 1 above are added. 32 mg of the expected product are thus obtained.

EXAMPLE 15

Trans-N2-(4-aminocyclohexyl)-N6-(4-chlorophenyl)-9H-purine-2,6-diamine

Stage 1: 2-chloro-N-(4-chlorophenyl)-9H-purin-6-amine

The procedure is carried out as in Example 1, starting with 472.5 mg of 2,6-dichloropurine, 5 ml of butanol and 398.0 mg of para-chloroaniline. 700.3 mg of the expected product are thus obtained.

Stage 2: Trans-N2-(4-aminocyclohexyl)-N6-(4-chlorophenyl)-9H-purine-2,6-diamine 2850 mg of trans-1,4-diaminocyclohexane are heated to its melting point (70° C.) and 2260 mg of the product obtained in stage 1 above are added. 80 mg of the expected product are thus obtained.

EXAMPLE 16 trans-N2-(4-aminocyclohexyl)-N6-(3,4-dichlorophenyl)-9H-purine-2,6-diamine

Stage 1: 2-chloro-N-(3,4-dichlorophenyl)-9H-purin-6-amine

The procedure is carried out as in Example 1, starting with 472.5 mg of 2,6-dichloropurine, 5 ml of butanol and 505.5 mg of metapara-3,4-dichloroaniline. 786.4 mg of the expected product are thus obtained.

Stage 2: Trans-N2-(4-aminocyclohexyl)-N6-(3,4-dichlorophenyl)-9H-purine-2,6-diamine 2850 mg of trans-1,4-diaminocyclohexane are heated to its melting point (70° C.) and 2140 mg of the product obtained in stage 1 above are added. 50 mg of the expected product are thus obtained.

EXAMPLE 17

Butyl trans-4-[[2-[(4-aminocyclohexyl)amino]-9H-purin-6-yl]amino]benzoate

Stage 1: Butyl 4-[(2-chloro-9H-purin-6-yl)amino]benzoate

The procedure is carried out as in Example 1, starting with 472.5 mg of 2,6-dichloropurine, 5 ml of butanol and 602.9 mg of butyl 4-aminobenzoate. 864.5 mg of the expected product are thus obtained.

Stage 2: Butyl trans-4-[[2-[(4-aminocyclohexyl)amino]-9H-purin-6-yl]amino]benzoate 2850 mg of trans-1,4-diaminocyclohexane are heated to its melting point (70° C.) and 2190 mg of the product obtained in stage 1 above are added. 60 mg of the expected product are thus obtained.

EXAMPLE 18

2-(diethylamino)ethyl trans-4-[[2-[(4-aminocyclohexyl)amino]-9H-purin-6-yl]amino]benzoate Stage 1: 2-(diethylamino)ethyl 4-[(2-chloro-9H-purin-6-yl)amino]benzoate The procedure is carried out as in Example 1, starting with 472.5 mg of 2,6-dichloropurine, 5 ml of butanol and 737.3 mg of 2-(N,N-diethylamino)ethyl 4-amino-benzoate. 972.2 mg of the expected product are thus obtained.

Stage 2: 2-(diethylamino)ethyl trans-4-[[2-[(4-aminocyclohexyl)amino]-9H-purin-6-yl]amino]benzoate 2850 mg of trans-1,4-diaminocyclohexane are heated to its melting point (70° C.) and 2440 mg of the product obtained in step 1 above are added. 30 mg of the expected product are thus obtained.

EXAMPLE 19

Trans-4-[[2-[(4-aminocyclohexyl)amino]-9H-purin-6-yl]amino]-N-phenylbenzamide

Stage 1: 4-[(2-chloro-9H-purin-6-yl]amino]-N-phenylbenzamide

The procedure is carried out as in Example 1, starting with 195 mg of 2,6-dichloropurine, 5 ml of butanol and 272 mg of 4-amino-N-phenylbenzamide. 360 mg of the expected product are thus obtained.

Stage 2: Trans-4-[[2-[(4-aminocyclohexyl)amino]-9H-purin-6-yl]amino]-N-phenylbenzamide 937 mg of trans-1,4-diaminocyclohexane are heated to its melting point (70° C.) and 300 mg of the product obtained in stage 1 above are added. 35 mg of the expected product are thus obtained.

EXAMPLE 20

Trans-N2-(4-aminocyclohexyl)-N6-[4-(dimethylamino)phenyl]-9H-purine-2,6-diamine

Stage 1: 2-chloro-N-[4-(dimethylamino)phenyl]-9H-purin-6-amine

The procedure is carried out as in Example 1, starting with 378 mg of 2,6-dichloropurine, 5 ml of butanol and 300 mg of N,N-dimethyl-p-phenylenediamine. 494 mg of the expected product are thus obtained.

Stage 2: Trans-N2-(4-aminocyclohexyl)-N6-[4-(dimethylamino)phenyl]-9H-purine-2,6-diamine 1200 mg of trans-1,4-diaminocyclohexane are heated to its melting point (70° C.) and 432 mg of the product obtained in stage 1 above are added. 65 mg of the expected product are thus obtained.

EXAMPLE 21

Trans-4-[[2-[(4-aminocyclohexyl)amino]-9H-purin-6-yl]amino]benzaldehyde

Stage 1 4-[(2-chloro-9H-purin-6-yl)amino]benzaldehyde

The procedure is carried out as in Example 1, starting with 189 mg of 2,6-dichloropurine, 5 ml of butanol and 149 mg of 4-aminoacetophenone. 308 mg of the expected product are thus obtained.

Stage 2 Trans-4-[[2-[(4-aminocyclohexyl)amino]-9H-purin-6-yl]amino]benzaldehyde 300 mg of trans-1,4-diaminocyclohexane are heated to its melting point (70° C.) and 288 mg of the product obtained in stage 1 above are added. 35 mg of the expected product are thus obtained.

EXAMPLE 22

Trans-4-[[2-[(4-aminocyclohexyl)amino]-9H-purin-6-yl]amino]benzamide

Stage 1: 4-[(2-chloro-9H-purin-6-yl)amino]benzamide

The procedure is carried out as in Example 1, starting with 189 mg of 2,6-dichloropurine, 5 ml of butanol and 150 mg of 4-aminobenzamide. 329 mg of the expected product are thus obtained.

Stage 2: Trans-4-[[2-[(4-aminocyclohexyl)amino]-9H-purin-6-yl]amino]benzamide 800 mg of trans-1,4-diaminocyclohexane are heated to its melting point (70° C.) and 289 mg of the product obtained in stage 1 above are added. 147 mg of the expected product are thus obtained.

EXAMPLE 23

Ethyl 4-[[2-[[4-(ethoxycarbonyl)phenyl]amino]-9H-purin-6-yl]amino]benzoate

The procedure is carried out as in stage 2 of Example 1, using 238 mg of the product obtained in stage 1 of Example 1 and 660 mg of ethyl 4-aminobenzoate in place of trans-1,4-diaminocyclohexane. 181 mg of the expected product are thus obtained.

EXAMPLE 24

Ethyl 4-[[2-[(3-nitrophenyl)amino]-9H-purin-6-yl]amino]benzoate

The procedure is carried out as in stage 2 of Example 1, using 238 mg of the product obtained in stage 1 of Example 1 and 520 mg of 3-nitroaniline in place of trans-1,4diaminocyclohexane. 170 mg of the expected product are thus obtained.

EXAMPLE 25

Ethyl 4-[[2-[(3-aminophenyl)amino]-9H-purin-6-yl]amino]benzoate 214 mg of the product of Example 24 are treated with 95 mg of platinum oxide ($PtO_2$) in a mixture of 2.6 ml of ethyl acetate and 2.6 ml of methanol in the presence of hydrogen, $H_2$. 78 mg of the expected product are thus obtained.

EXAMPLE 26

Ethyl 4-[[2-[[(4-dimethylamino)phenyl]amino]-9H-purin-6-yl]amino]benzoate

The procedure is carried out as in stage 2 of Example 1, using 238 mg of the product obtained in stage 1 of Example 1 and 520 mg of N,N-dimethyl-p-phenylenediamine in place of trans-1,4-diaminocyclohexane. 65 mg of the expected product are thus obtained.

EXAMPLE 27

Ethyl 4-[[2-(cyclohexylamino)-9H-purin-6-yl]amino]benzoate

The procedure is carried out as in stage 2 of Example 1, using 238 mg of the product obtained in stage 1 of Example 1 and 0.86 ml of cyclohexylamine in place of trans-1,4-diaminocyclohexane. 121 mg of the expected product are thus obtained.

EXAMPLE 28

Ethyl 4-[[2-[[3-(ethoxycarbonyl)phenyl]amino]-9H-purin-6-yl]amino]benzoate

The procedure is carried out as in stage 2 of Example 1, using 238 mg of the product obtained in stage 1 of Example 1 and 567 mg of 3-methylaminobenzoate in place of trans-1,4-diaminocyclohexane. 305 mg of the expected product are thus obtained.

EXAMPLE 29

Pharmaceutical Composition

Tablets corresponding to the following formula were prepared:

| Product of Example 1 | 0.2 g |
|---|---|
| Excipient for a finished tablet at | 1 g |

(Details of the excipient: lactose, talc, starch, magnesium stearate.)

Pharmacological Part:

1) Test of Inhibition of the Activity of CIV-CDK (CIV1)

a) Preparation of the Reagents

-(1)- 3× Enzyme Cocktail
  967 µl Buffer [50 mM Tris-HCl-0.1 M NaCl-pH 7.5]
  -0.1% BSA+30 µl Cdk2 (1 mg/ml)
  +3 µl CaCiv1 (0.4 mg/ml)

Specify Origin of CIV1

-(2)- 3× Inhibitor Cocktail
  Prepare a 3× range of inhibitor in 3% of DMSO-Buffer [50 mM Tris-HCl-0.1 M NaCl-pH 7.5]-0.1% BSA
  Example of range: 200; 100; 30; 20; 10; 3; 2; 1; 0.3; 0 µM -(3)- 3× ATP Cocktail
  12.2 µl [$^{33}$P]ATP+305 µl 10× kinase Buffer+700 µl Water
  10× kinase Buffer=0.5 M Tris-0.1 M MgCl2-1 mM Na3VO4-10 mM DTT-15 µM
  ATP-pH 7.5+1 tablet of protease inhibitors (Complete EDTA Free™) per 5 ml of Buffer b) Carrying Out of the Test 1)—mix 30 µl of the 3× enzyme cocktail (1) with 30 µl of the 3× inhibitor cocktail (2)

2)—add 30 µl of the 3× ATP cocktail (3) (start of the reaction)

3)—incubate for 30 min at room temperature (20 to 25° C.)

4)—stop the reaction by adding 250 µl of Buffer [50 mM Tris-HCl-0.1 M NaCl-pH 7.5]-0.1% BSA-25 mM EDTA 5)—distribute 100 µl into a plate coated with antibodies directed against the reaction substrate 6)—incubate for 60 min at room temperature, stirring gently and then wash 3 times with 300 µl
  Buffer [50 mM Tris-HCl-0.1 M NaCl-pH 7.5]-0.05% Tween20

9)—Place the plate to dry for 30 min at 37° C.

10)—Place for counting in a scintillation counter c) Results Obtained, Expressed as $IC_{50}$ Expressed in Micromolar

| Product | $IC_{50}$ in micromolar |
|---|---|
| Example 1 | 0.5 |
| Example 11 | 2.5 |
| Example 14 | 2.0 |
| Example 16 | 2.9 |
| Example 17 | 5.6 |

-continued

| Product | IC$_{50}$ in micromolar |
|---|---|
| Example 18 | 4.3 |
| Example 19 | 3.82) MIC test Candida albicans |

A constant number of cells of a given strain are exposed to increasing concentrations of an antifungal, under conditions taken from NCCLS (National Committee for Clinical Laboratory Standards, 1997 [reference method for broth dilution antifungal susceptibility testing of yeasts]. Approved Standard M27-A. NCCLS, Villanova, Pa.); the minimum concentration with which a visible reduction in the cloudiness from cell growth was observed (at least 80% relative to a control with no product) is the minimum inhibitory concentration (MIC) of the antifungal for the test strain.

Supplement the L-glutamine-free RPMI 1640 medium (liquid) with L-glutamine (0.3 g/l or 10.5 ml of a solution at 200 mM) and buffer with 34.54 g/l (0.165 M) of M morpholinepropanesulfonic acid (MOPS). Sterilize the medium by filtration. Distribute 100 µl of RPMI medium into each well of a 96-well microplate. Distribute the appropriate volume of the antifungal solution in the first column of the microplate and adjust with medium to 200 µl. Carry out a 2-fold serial dilution in order to establish a range of 11 concentrations in each lane of the microplate. The 12th well of each row will serve as a control for growth. Prepare the cellular suspension from a (liquid or agar) culture or from a frozen vial, dilute it in RPMI medium in order to obtain a cellular suspension at 5×10$^3$–2×10$^4$ cells/ml. Distribute 100 µl of the cellular suspension into the microplate. The MIC for all the Candida species was read after 24–48 h, for *Cryptococcus* and *Aspergillus* after 48–72 h of incubation at 37° C. in a normal atmosphere. The MIC is read by visual readings by determining the well which contains the lowest dose of antifungal which causes an inhibition of at least 80% of the growth of the fungus.

| Product | MIC in µg/ml |
|---|---|
| 15 | 100 |
| 16 | 25 |
| 17 | 12.5 |

The invention claimed is:

1. A compound selected from the group consisting of:
ethyl trans-4-[[2-[(4-aminocyclohexyl)amino]-1H-purin-6-yl]amino]benzoate dihydrochloride;
trans-N2-(4-aminocyclohexyl)-N6-(2-aminoethyl)-1H-purine-2,6-diamine trihydrochloride;
trans-N2-(4-aminocyclohexyl)-N6-propyl-1H-purine-2,6-diamine dihydrochloride;
trans-N2-(4-aminocyclohexyl)-N6-(phenylmethyl)-1H-purine-2,6-diamine dihydrochloride;
trans-N2-(4-aminocyclohexyl)-N6-(4-methoxyphenyl)-1H-purine-2,6-diamine dihydrochloride;
trans-N2-(4-aminocyclohexyl)-N6-[4-(trifluoromethoxy)phenyl]-1H-purine-2,6-diamine dihydrochloride;
trans-N2-(4-aminocyclohexyl)-N6-[1-(phenylmethyl)-4-piperidinyl]-1H-purine-2,6-diamine trihydrochloride;
trans-N2-(4-aminocyclohexyl)-N6-[2-[(phenylmethyl)amino]ethyl]-1H-purine-2,6-diamine trihydrochloride;
trans-N2-(4-aminocyclohexyl)-N6-[(3,4-dimethoxyphenyl)methyl]-1H-purine-2,6-diamine;
trans-N2-(4-aminocyclohexyl)-1H-purine-2,6-diamine dihydrochloride;
trans-N2-(4-aminocyclohexyl)-N6-[4-phenyl]-1H-purine-2,6-diamine dihydrochloride;
trans-N2-(4-aminocyclohexyl)-N6-(4-fluorophenylmethyl)-1H-purine-2,6-diamine;
trans-N2-(4-aminocyclohexyl)-N6-[1-(ethoxycarbonyl)-4-piperidinyl]-1H-purine-2,6-diamine;
ethyl trans-3-[[2-[(4-aminocyclohexyl)amino]-9H-purin-6-yl]amino]benzoate;
trans-N2-(4-aminocyclohexyl)-N6-(4-chlorophenyl)-9H-purine-2,6-diamine;
trans-N2-(4-aminocyclohexyl)-N6-(3,4-dichlorophenyl)-9H-purine-2,6-diamine;
butyl trans-4-[[2-[(4-aminocyclohexyl)amino]-9H-purin-6-yl]amino]benzoate;
2-(diethylamino)ethyl trans-4-[[2-[(4-aminocyclohexyl)amino]-9H-purin-6-yl]amino]benzoate;
trans-4-[[2-[(4-aminocyclohexyl)amino]-9H-purin-6-yl]amino]-N-phenylbenzamide;
trans-N2-(4-aminocyclohexyl)-N6-[4-(dimethylamino)phenyl]-9H-purine-2,6-diamine;
trans-4-[[2-[(4-aminocyclohexyl)amino]-9H-purin-6-yl]amino]benzaldehyde;
trans-4-[[2-[(4-aminocyclohexyl)amino]-9H-purin-6-yl]amino]benzamide;
ethyl 4-[[2-[[4-(ethoxycarbonyl)phenyl]amino]-9H-purin-6-yl]amino]benzoate;
ethyl 4-[[2-[(3-nitrophenyl)amino]-9H-purin-6-yl]amino]benzoate;
ethyl 4-[[2-[(3-aminophenyl)amino]-9H-purin-6-yl]amino]benzoate;
ethyl 4-[[2-[[(4-dimethylamino)phenyl]amino]-9H-purin-6-yl]amino]benzoate;
ethyl 4-[[2-(cyclohexylamino)-9H-purin-6-yl]amino]benzoate; and;
ethyl 4-[[2-[[3-(ethoxycarbonyl)phenyl]amino]-9H-purin-6-yl]amino]benzoate.

2. A compound of claim 1 selected from the group consisting of
ethyl trans-4-[[2-[(4-aminocyclohexyl)amino]-1H-purin-6-yl]amino]benzoate dihydrochloride;
trans-N2-(4-aminocyclohexyl)-N6-[4-phenyl]-1H-purine-2,6-diamine dihydrochloride;
ethyl trans-3-[[2-[(4-aminocyclohexyl)amino]-9H-purin-6-yl]amino]benzoate;
trans-N2-(4-aminocyclohexyl)-N6-(3,4-dichlorophenyl)-9H-purine-2,6-diamine;
butyl trans-4-[[2-[(4-aminocyclohexyl)amino]-9H-purin-6-yl]amino]benzoate;
2-(diethylamino)ethyl trans-4-[[2-[(4-aminocyclohexyl)amino]-9H-purin-6-yl]amino]benzoate; and;
trans-4-[[2-[(4-aminocyclohexyl)amino]-9H-purin-6-yl]amino]-N-phenylbenzamide.

3. An intermediate selected from the group consisting of

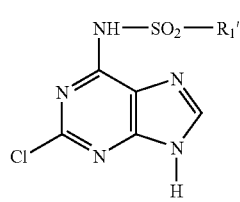 (IX)

in which $R_1'$ is selected from hydrogen, aryl, —$CH_2$-aryl, heterocyclic, —$CH_2$-heterocyclic, alkyl, and —$SO_2$-alkyl;

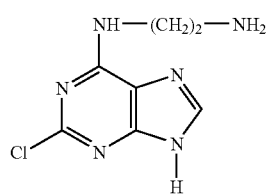 (X)

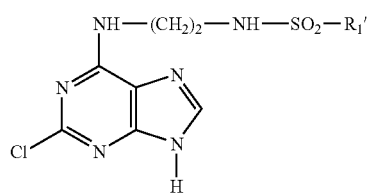 (XII)

in which $R_1'$ is selected from hydrogen, aryl, —$CH_2$-aryl, heterocyclic, —$CH_2$-heterocyclic, alkyl, and —$SO_2$-alkyl;

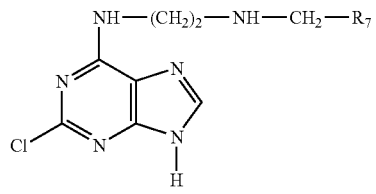 (XIII)

in which $R_7$ is selected from aryl, heterocyclic and alkyl;

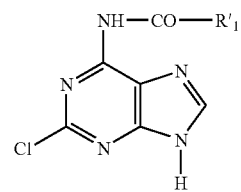 ($M_1$)

in which $R'_1$ is selected from hydrogen, aryl, —$CH_2$-aryl, heterocyclic, —$CH_2$-heterocyclic, alkyl, and —$SO_2$-alkyl;

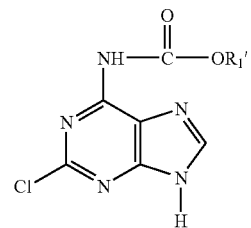 ($M_2$)

in which $R_1'$ is selected from hydrogen, aryl, —$CH_2$-aryl, heterocyclic, —$CH_2$-heterocyclic, alkyl, and —$SO_2$-alkyl; and

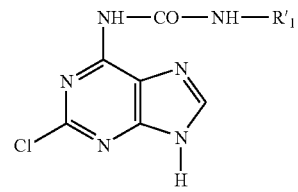 ($M_3$)

in which $R_1'$ is selected from hydrogen, aryl, —$CH_2$-aryl, heterocyclic, —$CH_2$-heterocyclic, alkyl, and —$SO_2$-alkyl.

* * * * *